(12) United States Patent
Hanson et al.

(10) Patent No.: US 6,174,923 B1
(45) Date of Patent: *Jan. 16, 2001

(54) USE OF ETHYNYL ALANINE AMINO DIOL COMPOUNDS FOR TREATMENT OF RENIN-MEDIATED DISORDERS

(75) Inventors: Gunnar J. Hanson, Skokie; John S. Baran, Winnetka, both of IL (US)

(73) Assignee: G. D. Searle & Co., Chicago, IL (US)

( * ) Notice: Under 35 U.S.C. 154(b), the term of this patent shall be extended for 0 days.

This patent is subject to a terminal disclaimer.

(21) Appl. No.: 09/239,493

(22) Filed: Jan. 28, 1999

Related U.S. Application Data

(63) Continuation of application No. 09/046,882, filed on Mar. 24, 1998, now Pat. No. 5,942,548, which is a continuation of application No. 08/783,954, filed on Jan. 16, 1997, now abandoned, which is a continuation of application No. 08/586,440, filed on Jan. 16, 1996, now abandoned, which is a continuation of application No. 08/199,211, filed on Feb. 23, 1994, now Pat. No. 5,484,811, which is a continuation of application No. PCT/US92/08842, filed on Oct. 22, 1992, which is a continuation of application No. 07/783,955, filed on Oct. 29, 1991, now Pat. No. 5,227,401.

(51) Int. Cl.$^7$ .................................................. A61K 31/165
(52) U.S. Cl. ..................... 514/616; 514/252.12; 514/315; 514/317; 514/357; 514/365; 514/374; 514/378; 514/400; 514/427; 514/428; 514/489; 514/517; 514/588; 514/595; 514/601; 514/608
(58) Field of Search ............................................. 514/616

(56) References Cited

U.S. PATENT DOCUMENTS

| | | | |
|---|---|---|---|
| 5,227,401 | * | 7/1993 | Hanson et al. ........................ 514/489 |
| 5,484,811 | * | 1/1996 | Hanson et al. ........................ 514/489 |
| 5,942,548 | * | 8/1999 | Hanson et al. ........................ 514/616 |

\* cited by examiner

Primary Examiner—Richard L. Raymond

(74) Attorney, Agent, or Firm—J. Timothy Keane

(57) ABSTRACT

Compounds characterized generally as ethynyl alanine amino diol derivatives are useful to treat disorders mediated by plasma renin activity. Compounds of particular interest are renin inhibitors of Formula I

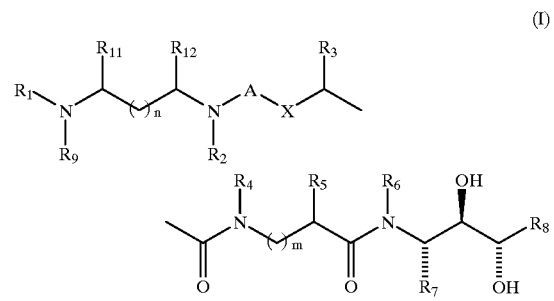

wherein A is selected from CO and $SO_2$ wherein X is selected from oxygen atom and methylene; wherein each of $R_1$ and $R_9$ is a group independently selected from hydrido, methyl, ethyl, n-propyl, isopropyl, benzyl, $\beta,\beta,\beta$-trifluoroethyl, t-butyloxycarbonyl and methoxymethylcarbonyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, cyclohexylmethyl, phenethyl, imidazolemethyl, pyridylmethyl and 2-pyridylethyl; wherein $R_5$ is propargyl or a propargyl-containing moiety; wherein $R_7$ is cyclohexylmethyl; wherein each of $R_4$ and $R_6$ is independently selected from hydrido and methyl; wherein $R_8$ is selected from ethyl, n-propyl, isobutyl, cyclopropyl, cyclobutyl, cyclopentyl, cyclohexyl, cyclopropylmethyl, cyclohexylmethyl, cyclohexylethyl, allyl, vinyl and fluorovinyl; wherein each of $R_{11}$ and $R_{12}$ is independently selected from hydrido, alkyl and phenyl; wherein m is zero; and wherein n is a number selected from zero through three; or a pharmaceutically-acceptable salt thereof.

11 Claims, No Drawings

USE OF ETHYNYL ALANINE AMINO DIOL COMPOUNDS FOR TREATMENT OF RENIN-MEDIATED DISORDERS

This is a continuation of application Ser. No. 09/046,882, filed on Mar. 24, 1998, now U.S. Pat. No. 5,942,548, which is a continuation of application Ser. No. 08/783,954 filed on Jan. 16, 1997 now abandoned, which is a continuation of application Ser. No. 08/586,440 filed on Jan. 16, 1996 now abandoned, which is a continuation of application Ser. No. 08/199,211, filed Feb. 23, 1994, now issued as U.S. Pat. No. 5,484,811, which is a continuation of PCT/US92/08842, filed on Oct. 22, 1992, which is a continuation of Ser. No. 07/783,955 filed on Oct. 29, 1991, now issued as U.S. Pat. No. 5,227,401 of Gunnar J. Hanson and John S. Baran entitled ETHYNYL ALANINE AMINO DIOL COMPOUNDS FOR TREATMENT OF HYPERTENSION.

FIELD OF THE INVENTION

Renin-inhibiting compounds are known for control of hypertension. Of particular interest herein are compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot.* (*Tokyo*), 23, 259–262 (1970)]. This peptide, known as pepstatin, was found to reduce blood pressure in vivo after the injection of hog renin into nephrectomized rats [Gross et al, *Science*, 175, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger et al, *Nature*, 303, 81 (1983)]. High molecular weight peptides are generally considered undesirable as drugs because gastrointestinal absorption is impaired and plasma stability is compromised.

Short peptide aldehydes have been reported as renin inhibitors [Kokubu et al, *Biochim. Biophys. Res. Commun.*, 118, 929 (1984); Castro et al, *FEBS Lett.*, 167, 273 (1984)]. Such compounds have a reactive C-terminal aldehyde group and would likely be unstable in vivo.

Other peptidyl compounds have been described as renin inhibitors. EP Appl. #128,762, published Dec. 18, 1984, describes dipeptide and tripeptide glyco-containing compounds as renin inhibitors [also see Hanson et al, *Biochm.* *Biophys. Res. Comm.*, 132, 155–161 (1985), 146, 959–963 (1987)]. EP Appl. #181,110, published May 14, 1986, describes dipeptide histidine derivatives as renin inhibitors. EP Appl. #186,977 published Jul. 9, 1986 describes renin-inhibiting compounds containing an alkynyl moiety, specifically a propargyl glycine moiety, attached to the main chain between the N-terminus and the C-terminus, such as N-[4(S)-[(N)-[bis(1-naphthylmethyl)acetyl]-DL-propargylglycylamino]-3(S)-hydroxy-6-methylheptanoyl]-L-isoleucinol. EP Appl. #189,203, published Jul. 30, 1986, describes peptidyl-aminodiols as renin inhibitors. EP Appl. #200,406, published Dec. 10, 1986, describes alkylnaphthylmethylpropionyl-histidyl aminohydroxy alkanoates as renin inhibitors. EP Appl. #216,539, published Apr. 1, 1987, describes alkylnaphthylmethylpropionyl aminoacyl aminoalkanoate compounds as renin inhibitors orally administered for treatment of renin-associated hypertension. EP Appl. #229,667, published Jul. 22, 1987, describes acyl α-aminoacyl aminodiol compounds having a piperazinylcarbonyl or an alkylaminoalkylcarbonyl terminal group at the N-amino acid terminus, such as 2(S)-{[(1-piperazinyl)carbonyl]-oxy}-3-phenylpropionyl}-Phe-His amide of 2(S)-amino-1-cyclohexyl-3(R), 4(S)-dihydroxy-6-methylheptane. PCT Application No. WO 87/04349, published Jul. 30, 1987, describes aminocarbonyl aminoacyl hydroxyether derivatives having an alkylamino-containing terminal substituent and which are described as having renin-inhibiting activity for use in treating hypertension. EP Appl. #300,189 published Jan. 25, 1989 describes amino acid monohydric derivatives having an alkylamino-alkylamino N-terminus and a β-alanine-histidine or sarcosyl-histidine attached to the main chain between the N-terminus and the C-terminus, which derivatives are mentioned as useful in treating hypertension. U.S. Pat. No. 4,902,706 which issued Feb. 13, 1990 describes a series of histidineamide-containing amino alkylaminocarbonyl-H-terminal aminodiol derivatives for use as renin inhibitors. U.S. Pat. No. 5,032,577 which issued Jul. 16, 1991 describes a series of histidineamide-aminodiol-containing renin inhibitors.

DESCRIPTION OF THE INVENTION

Ethynyl alanine amino diol compounds, having utility as renin inhibitors for treatment of hypertension in a subject, constitute a family of compounds of general Formula I:

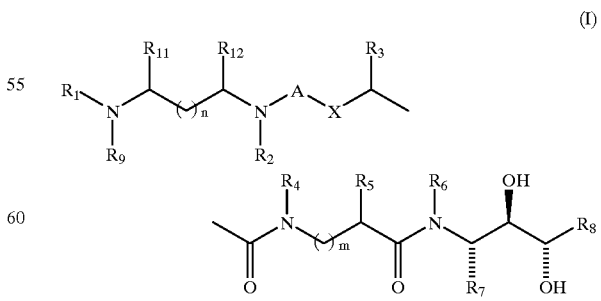

wherein A is selected from methylene, CO, SO and $SO_2$; wherein X is selected from oxygen atom, methylene and

with R₁₀ selected from hydrido, alkyl and benzyl; wherein each of $R_1$ and $R_9$ is a group independently selected from hydrido, alkyl, cycloalkyl, alkoxyacyl, haloalkyl, alkoxycarbonyl, benzyloxycarbonyl, loweralkanoyl, haloalkylacyl, phenyl, benzyl, naphthyl, and naphthylmethyl, any one of which groups having a substitutable position may be optionally substituted with one or more radicals selected from alkyl, alkoxy, alkenyl, alkynyl, halo, haloalkyl, cyano and phenyl, and wherein the nitrogen atom to which $R_1$ and $R_9$ are attached may be combined with oxygen to form an N-oxide; wherein $R_2$ is selected from hydrido, alkyl, dialkylaminoalkyl, alkylacylaminoalkyl, benzyl and cycloalkyl; wherein $R_3$ is selected from alkyl, cycloalkylalkyl, acylaminoalkyl, phenylalkyl, naphthylmethyl, aryl, heterocyclicalkyl and heterocycliccycloalkyl, wherein the cyclic portion of any of said phenylalkyl, naphthylmethyl, aryl, heterocyclicalkyl and heterocycliccycloalkyl groups may be substituted by one or more radicals selected from halo, hydroxy, alkoxy and alkyl; wherein each of $R_4$ and $R_6$ is independently selected from hydrido, alkyl, benzyl and cycloalkyl; wherein $R_5$ is selected from

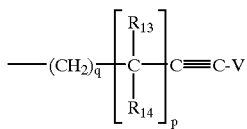

wherein V is selected from hydrido, alkyl, cycloalkyl, haloalkyl, benzyl and phenyl; wherein each of $R_{13}$ and $R_{14}$ is a radical independently selected from hydrido, alkyl, alkenyl, alkynyl, cycloalkyl, phenyl, heterocyclic, heterocyclicalkyl and heterocycliccycloalkyl; wherein $R_7$ is selected from substituted or unsubstituted alkyl, cycloalkyl, phenyl, cycloalkylalkyl and phenylalkyl, any one of which may be substituted with one or more groups selected from alkyl, hydroxy, alkoxy, halo, haloalkyl, alkenyl, alkynyl and cyano; wherein $R_8$ is selected from hydrido, alkyl, haloalkyl, alkylcycloalkyl, cycloalkyl, cycloalkylalkyl, hydroxyalkyl, alkenyl, alkylcycloalkenyl and alkoxycarbonyl; wherein each of $R_{11}$ and $R_{12}$ is independently selected from hydrido, alkyl, haloalkyl, dialkylamino and phenyl; and wherein m is zero or one; wherein n is a number selected from zero through five; wherein p is a number selected from zero through five; and wherein q is a number selected from zero through five; or a pharmaceutically-acceptable salt thereof.

A preferred family of compounds consists of compounds of Formula I wherein A is selected from methylene, CO, SO and $SO_2$; wherein X is selected from oxygen atom, methylene and

with $R_{10}$ selected from hydrido, alkyl and benzyl; wherein each of $R_1$ and $R_9$ is independently selected from hydrido, lower alkyl, haloalkyl, cycloalkyl, alkoxycarbonyl, benzyloxycarbonyl, loweralkanoyl, alkoxyacyl, phenyl and benzyl, and wherein the nitrogen atom to which $R_1$ and $R_9$ are attached may be combined with oxygen to form an N-oxide; wherein each of $R_2$, $R_4$ and $R_6$ is independently selected from hydrido and alkyl; wherein $R_3$ is selected from phenylalkyl, naphthylmethyl, cyclohexylalkyl, cyclopentylalkyl, heteroarylalkyl and heteroarylcycloalkyl; wherein $R_5$ is selected from

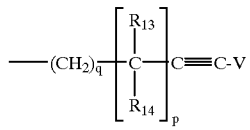

wherein V is selected from hydrido, alkyl, haloalkyl, benzyl and phenyl; wherein each of $R_{13}$ and $R_{14}$ is a radical independently selected from hydrido, alkyl, alkenyl, alkynyl, cycloalkyl, heteroaryl, heteroarylalkyl and heteroarylcycloalkyl; wherein $R_7$ is selected from substituted or unsubstituted cyclohexylmethyl and benzyl, either one of which may be substituted with one or more groups selected from alkyl, hydroxy, alkoxy, halo and haloalkyl; wherein $R_8$ is selected from hydrido, methyl, ethyl, n-propyl, n-butyl, isobutyl, cycloalkyl, cycloalkylalkyl, hydroxyalkyl, alkenyl, fluoroalkenyl and fluoroalkyl; wherein each of $R_{11}$ and $R_{12}$ is independently selected from hydrido, alkyl, dialkylamino and phenyl; wherein m is zero or one; wherein n is a number selected from zero through five; wherein p is a number selected from zero through five; and wherein q is a number selected from zero through five; or a pharmaceutically-acceptable salt thereof.

A more preferred family of compounds consists of compounds of Formula I wherein A is selected from methylene, CO, SO and $SO_2$; wherein X is selected from oxygen atom, methylene and

with $R_{10}$ selected from hyrido, alkyl and benzyl; wherein each of $R_1$ and $R_9$ is independently selected from hydrido, alkyl, alkoxyacyl, haloalkyl, alkoxycarbonyl, benzyloxycarbonyl, and benzyl, and wherein the nitrogen atom to which $R_1$ and $R_9$ are attached may be combined with oxygen to form an N-oxide; wherein each of $R_2$, $R_4$ and $R_6$ is independently selected from hydrido and alkyl; wherein $R_3$ is selected from benzyl, phenethyl, cyclohexylmethyl, phenpropyl, pyrrolidinyl, piperidinyl, pyrrolidinylmethyl, piperidinylmethyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, thiazolylcyclopropyl, imidazolecyclopropyl, thienylcyclopropyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_5$ is selected from

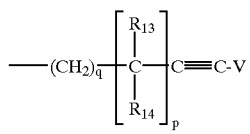

wherein V is selected from hydrido, alkyl and haloalkyl; wherein each of $R_{13}$ and $R_{14}$ is a radical independently selected from hydrido, alkyl, alkenyl, alkynyl, thiazole and thiazolemethyl; wherein $R_7$ is cyclohexylmethyl; wherein $R_8$ is selected from ethyl, n-propyl, isobutyl, cycloalkyl, cycloalkylalkyl, alkenyl, fluoroalkenyl and perfluoropropyl; wherein each of $R_{11}$ and $R_{12}$ is independently selected from hydrido, alkyl, dialkylamino and phenyl; wherein m is zero or one; wherein n is a number selected from zero through five; wherein p is a number selected from zero through five; and wherein q is a number selected from zero through five; or a pharmaceutically-acceptable salt thereof.

An even more preferred family of compounds consists of compounds Formula I wherein A is selected from CO and $SO_2$; wherein X is selected from oxygen atom, methylene and

with $R_{10}$ selected from hydrido and methyl; wherein each of $R_1$ and $R_9$ is independently selected from hydrido, lower alkyl, alkoxyacyl, alkoxycarbonyl, benzyloxycarbonyl, haloalkyl and benzyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, phenethyl, cyclohexylmethyl pyrrolidinyl, piperidinyl, pyrrolidinylmethyl, piperidinylmethyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, thiazolylcyclopropyl, imidazolecyclopropyl, thienylcyclopropyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein each of $R_4$ and $R_6$ is independently selected from hydrido and methyl; wherein $R_5$ is selected from

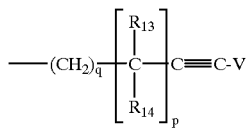

wherein V is selected from hydrido, alkyl and trifluoromethyl; wherein each of $R_{13}$ and $R_{14}$ is a radical independently selected from hydrido, alkyl and alkynyl; wherein $R_7$ is cyclohexylmethyl; wherein $R_8$ is independently selected from ethyl, n-propyl, isobutyl, cyclopropyl, cyclobutyl, cyclopentyl, cyclohexyl, cyclopropylmethyl, cyclobutylmethyl, cyclopentylmethyl, cyclopentylethyl, cyclohexylmethyl, cyclohexylethyl, allyl, vinyl and fluorovinyl; wherein each of $R_{11}$ and $R_{12}$ is independently selected from hydrido, alkyl, dialkylamino and phenyl; wherein m is zero; wherein n is a number selected from zero through five; wherein p is a number selected from zero through five; and wherein q is a number selected from zero through five; or a pharmaceutically-acceptable salt thereof.

A highly preferred family of compounds consists of compounds of Formula I wherein A is selected from CO and $SO_2$; wherein X is selected from oxygen atom and methylene; wherein each of $R_1$ and $R_9$ is independently selected from hydrido, methyl, ethyl, n-propyl, isopropyl, benzyl, $\beta,\beta,\beta$,-trifluoroethyl, t-butyloxycarbonyl and methoxymethylcarbonyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, cyclohexylmethyl, phenethyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_5$ is selected from

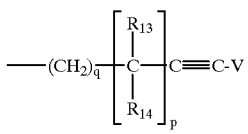

wherein V is selected from hydrido, alkyl and trifluoromethyl; wherein each of $R_{13}$ and $R_{14}$ is a radical independently selected from hydrido, methyl, ethyl, propyl and ethynyl; wherein $R_7$ is cyclohexylmethyl; wherein each of $R_4$ and $R_6$ is independently selected from hydrido and methyl; wherein $R_8$ is selected from ethyl, n-propyl, isobutyl, cyclopropyl, cyclobutyl, cyclopentyl, cyclohexyl, cyclopropylmethyl, cyclohexylmethyl, cyclohexylethyl, fluorovinyl, allyl and vinyl; wherein each of $R_{11}$ and $R_{12}$ is independently selected from hydrido, alkyl, dialkylamino and phenyl; wherein m is zero; wherein n is a number selected from zero through five; wherein p is a number selected from zero through five; and wherein q is a number selected from zero through five; or a pharmaceutically-acceptable salt thereof.

A more highly preferred class of compounds consists of compounds of Formula I wherein A is selected from CO and $SO_2$; wherein X is selected from oxygen atom and methylene; wherein each of $R_1$ and $R_9$ is a group independently selected from hydrido, methyl, ethyl, n-propyl, isopropyl, benzyl, $\beta,\beta,\beta$-trifluoroethyl, t-butyloxycarbonyl and methoxymethylcarbonyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, cyclohexylmethyl, phenethyl, imidazolemethyl, pyridylmethyl and 2-pyridylethyl; wherein $R_5$ is selected from

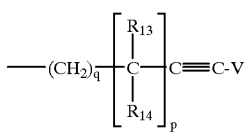

wherein V is selected from hydrido, alkyl and trifluoromethyl; wherein each of $R_{13}$ and $R_{14}$ is a radical independently selected from hydrido, methyl and ethynyl; wherein $R_7$ is cyclohexylmethyl; wherein each of $R_4$ and $R_6$ is independently selected from hydrido and methyl; wherein $R_8$ is selected from ethyl, n-propyl, isobutyl, cyclopropyl, cyclobutyl, cyclopentyl, cyclohexyl, cyclopropylmethyl, cyclohexylmethyl, cyclohexylethyl, allyl, vinyl and fluorovinyl; wherein each of $R_{11}$ and $R_{12}$ is independently selected from hydrido, alkyl and phenyl; wherein m is zero; wherein n is a number selected from zero through three; wherein p is a number selected from one through three; and wherein q is zero or one; or a pharmaceutically-acceptable salt thereof.

The term "hydrido" denotes a single hydrogen atom (H). This hydrido group may be attached, for example, to an oxygen atom to form a hydroxyl group; or, as another example, one hydrido group may be attached to a carbon atom to form a

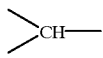

group; or, as another example, two hydrido groups may be attached to a carbon atom to form a —CH₂— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon—carbon double bond, which carbon—carbon double bond may have either cis or trans geometry within the alkenyl moiety. The term "alkynyl" embraces linear or branched radicals having two to about twenty carbon atoms, preferably two to about ten carbon atoms, and containing at least one carbon—carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenyl-ethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and SO₂. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. The term "heterocyclic", as used alone or within groups such as "heterocyclicalkyl", and "heterocycliccycloalkyl", (hereinafter referred to as "heterocyclic-containing groups") embraces radicals having a saturated, or partially unsaturated, or fully saturated heterocyclic group, wherein the cyclic portion consists of a ring system having one ring or two fused rings, which ring system contains one, two or three hetero atoms as ring members selected from nitrogen, oxygen and sulfur, and which ring system has 4 to about 12 ring members. Examples of saturated heterocyclic-containing groups are pyrrolidinyl, piperidinyl, pyrrolidinylmethyl, piperidinylmethyl, pyrrolidinylcyclopropyl and piperidinylcyclopropyl. The term "heteroaryl", whether used alone or within the greater terms "heteroarylalkyl" or "heteroarylcycloalkyl", denotes a subset of "heterocyclic-containing groups" having a cyclic portion which is fully-unsaturated, that is, aromatic in character, and which has one or two hetero atoms as ring members, said hetero atoms selected from oxygen, sulfur and nitrogen atoms, and which ring system has five or six ring members. The "heteroaryl" ring may be attached to a linear or branched alkyl radical having one to about ten carbon atoms or may be attached to a cycloalkyl radical having three to about nine carbon atoms. Examples of such heteroarylalkyl or heteroarylcycloalkyl groups are pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, thiazolylcyclopropyl, imidazolecyclopropyl, thienylcyclopropyl, isoxazolemethyl, isoxazoleethyl, pyridazinemethyl, pyridazineethyl, pyrazinemethyl and pyrazineethyl. The "heterocyclic" or "heteroaryl" portion of the radical, as well as the alkyl or cycloalkyl portion of groups containing a "heterocyclic" or "heteroaryl" portion, may be substituted at a substitutable position with one or more groups selected from oxo, alkyl, alkoxy, halo, haloalkyl, cyano, aralkyl, aralkoxy, aryl and aryloxy. Such "heterocyclic", "heterocyclic"-containing group, or "heteroaryl" group may be attached as a substituent through a carbon atom of the hetero ring system, or may be attached through a carbon atom of a moiety substituted on a hetero ring-member carbon atom, for example, through the methylene substituent of an imidazolemethyl moiety. Also, a heterocyclic or heterocyclic-containing group may be attached through a ring nitrogen atom. For any of the foregoing defined radicals, preferred radicals are those containing from one to about fifteen carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Also included in the family of compounds of Formula I are isomeric forms, including diastereoisomers, and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid.

Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. Also included within the phrase "pharmaceutically-acceptable salts" are "quaternary" salts or salts of "onium" cations, such as ammonium, morpholinium and piperazinium cations, as well as any substituted derivatives of these cations where the salt is formed on the nitrogen atom lone pair of electrons. All of these salts may be prepared by conventional means from the corresponding compound of Formula I by reacting, for example, the appropriate acid or base with the compound of Formula I.

Compounds of Formula I would be useful to inhibit enzymatic conversion of angiotensionogen to angiotensin I. When administered orally, a compound of Formula I would be expected to inhibit plasma renin activity and, consequently, lower blood pressure in a mammalian subject (e.g., a human subject). Thus, compounds of Formula I would be therapeutically useful in methods for treating hypertension by administering to a hypertensive subject a therapeutically-effective amount of a compound of Formula I. The phrase "hypertensive subject" means, in this context, a mammalian subject suffering from or afflicted by the effects of hypertension or susceptible to a hypertensive condition if not treated to prevent or control such hypertension.

Description on of the Synthetic Methods for the
Preparation of the Renin Inhibitors of the Invention

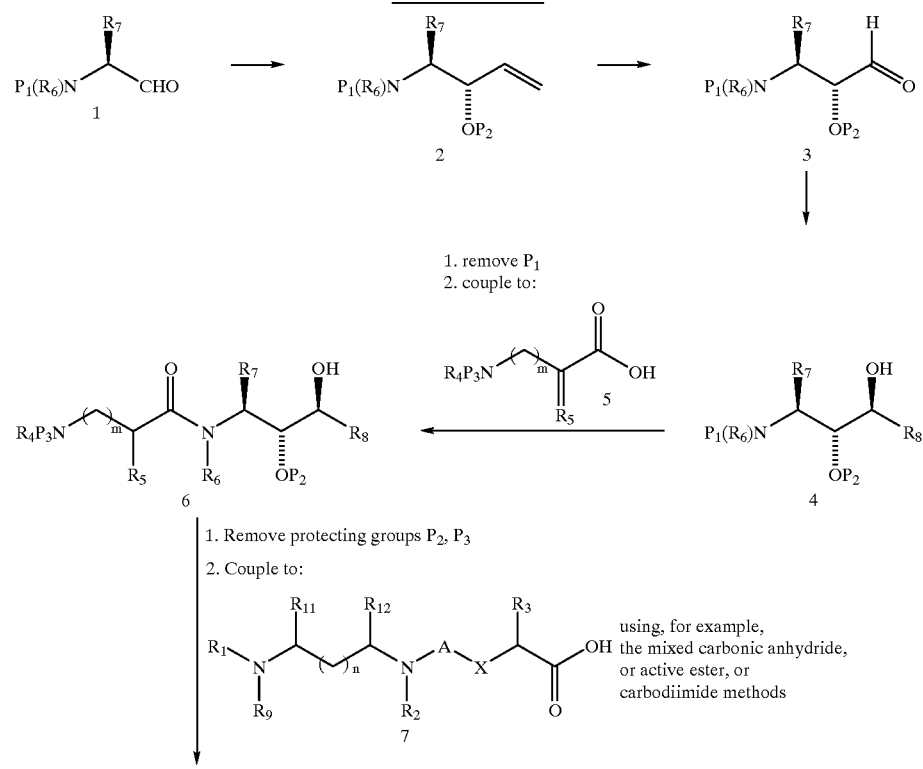

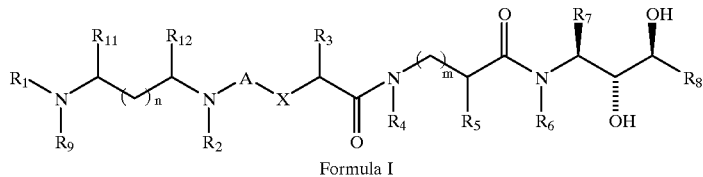

Formula I

Synthetic Scheme 1

Preparation of Compounds of Formula I

A suitably protected amino aldehyde 1 is treated with a Grignard reagent or other organometallic reagent, preferably vinylmagnesium bromide, to obtain the vinyl carbinol 2. This material, suitably protected, is oxidized, preferably with ozone, followed by dimethyl sulfide or zinc treatment, to give intermediate 3. The preceeding process is exemplified in Hanson, et al., J. Org. Chem. 50, 5399 (1985). This aldehyde is reacted with an organometallic reagent such as isobutylmagnesium chloride to give intermediate 4. Other suitable organometallic reagents include ethylmagnesium bromide, vinylmagnesium bromide, cyclopropylmagnesium bromide, and allylmagnesium bromide, but the choices are not limited to these reagents. After the formation of 4, further transformation of the added side chain is permitted, before going on the next depicted step. For example, the compound 4 derived from the addition of allylmagnesium bromide may be cyclopropanated via diazomethane and rhodium acetate, to give a cyclopropylmethyl side chain. Compound 4 is deprotected then coupled, using standard amide/peptide coupling methodology to protected triple bond-containing (ethynyl) amino acid derivatives 5 to give compound 6. These standard coupling procedures such as the carbodiimide, active ester (N-hydroxysuccinimide), and mixed carbonic anhydride methods are shown in Benoiton, et al. J. Org. Chem. 48, 2939 (1983) and Bodansky, et al. "Peptide Synthesis", Wiley (1976). Ethynyl-containing amino acid derivatives may be prepared by using procedures such as found in Schollkopf, Tetrahedron 39, 2085 (1983). Intermediate 6 is then deprotected, then coupled to intermediate 7 using the standard amide/peptide coupling methodology, to give compounds of Formula I. Suitable protecting groups may be selected from among those reviewed by R. Geiger in "The Peptides", Academic Press, N.Y. vol. 2 (1979). For example, $P_1$ may by Boc or Cbz; $P_2$ may be a typical oxygen protective group such as acetyl or t-butyldimethylsilyl.

Synthetic Scheme 2

Preparation of 7:

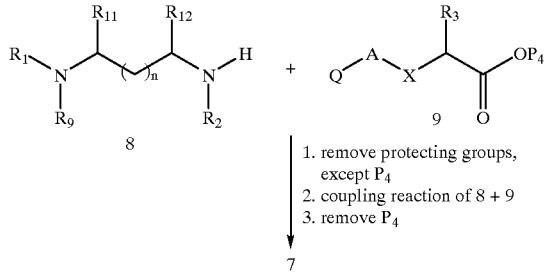

Synthetic Scheme 2

Preparation of Compounds of Formula I

Intermediate 7 may be prepared according to the schematic of Synthetic Scheme 2. Intermediate 7 is prepared by coupling amine 8 to mono-protected carboxylic acid 9. Carboxylic acid 9 is a mono-activated moiety by virtue of a suitable leaving group Q which may be chloride, bromide, fluoride, N-hydroxysuccinimido, p-toluenesulfonyloxy or isobutyloxycarbonyloxy, but is not limited to these groups. After coupling, protecting group $P_4$ is removed (if $P_4$ is a benzyl group, hydrogenolysis over palladium-on-carbon (Pd—C) is performed) to give intermediate amino acid 7.

Synthetic Scheme 3

Preparation of Intermediate 8

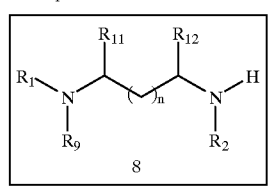

Preparation of 8, a non-cyclized diamine:

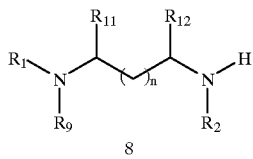

-continued

Preparation of 8:

8a:

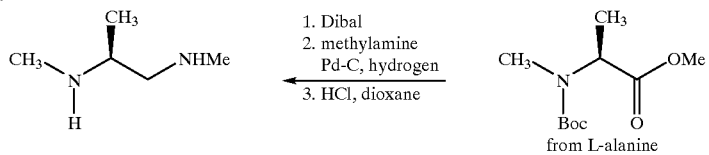

8b:

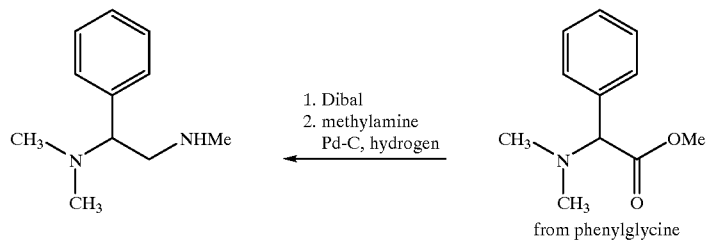

8c:

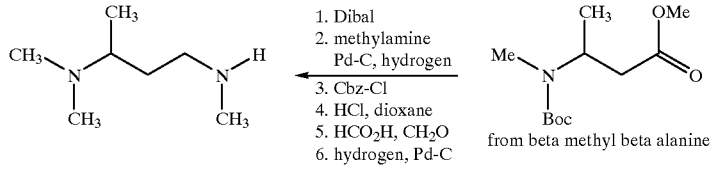

Synthetic Scheme 3

Preparation of Compounds of Formula I

Synthetic Scheme 3 describes the preparation of intermediate 8, a non-cyclic diamine. Many of the members of this class, such as ethylene diamine, N,N,N'-trimethylethylene diamine, N,N'-dimethylethylene diamine, N,N'-dimethylpropylene diamine, etc. are commercially available starting materials. Other substituted diamines such as compounds 8a through 8c are obtainable by the procedures depicted in Scheme 3. For example, Boc-L-alanine methyl ester is reduced with diisobutylaluminum hydride to give the corresponding aldehyde which is then reductively aminated with methylamine, then the Boc group is cleaved to give 8a. Alternatively, the procedure of Miller, et al. J. Med. Chem. 19, 1382 (1976) may be employed to give intermediate 8. In another example, a suitably protected diamine is treated with trifluoroacetaldehyde in the presence of sodium cyanoborohydride to give an trifluoroethyl substituent on nitrogen, followed by deprotection to give amine 8.

Abbreviations Used

P1 is an N-protecting group; P2 is H or an oxygen protecting group; P3 is an N-protecting group; P4 is an oxygen protecting group such as benzyl or methyl; Q is a leaving group; Boc is t-butyloxycarbonyl; Cbz is carbobenzoxy.

The following Steps 1–13 constitute specific exemplification of methods to prepare starting materials and intermediates embraced by the foregoing generic synthetic schemes. Those skilled in the art will readily understand that known variations of the conditions and processes of the following preparative procedures can be used to prepare the compounds of Steps 1–13. All temperatures expressed are in degrees Centigrade.

Compounds of Examples 1–3 were prepared by using the procedures described in the following Steps 1–13:

Step 1

(2R,3S)-N-[(tert-Butyloxy)carbonyl]-3-amino-2-acetoxy-4-phenylbutanal

Ozone/oxygen was bubbled at −70° C. into a solution of (3S,4S)-N-[(tert-Butyloxy)carbonyl]-4-amino-3-acetoxy-5-phenylpentene (2.55 g, 8.0 mmol) (prepared by the method of Hanson, et al., J. Org. Chem. 50, 5399 (1985)) in 100 mL of methylene chloride until a deep blue color persisted. Oxygen was introduced until the blue color completely faded, then 3.0 mL of Me$_2$S was added and the solution was allowed to warm to 0–5° C. and stand overnight. The solvent was removed at 0° C. under vacuum yielding the title compound as a thick yellow oil which was used in the following step without purification.

Step 2

(2S,3R,4S)-N-[(tert-Butyloxy)carbonyl]-2-amino-1-phenyl-3,4-dihydroxy-6-methylheptane The oil prepared in Step 1 was dissolved under nitrogen in 100 mL of dry THF and cooled to −70° C. To this solution was added 13 mL (26 mmol) of a 2.0M solution of isobutylmagnesium chloride in ether and the stirred mixture was allowed to warm to room temperature and stir for 2 hrs. After decomposition with MeOH/H$_2$O the mixture was diluted with ether, washed with saturated NH$_4$Cl solution twice, then dried and the solvents stripped off under vacuum. The residue was allowed to stand overnight in 80% MeOH—H$_2$O containing excess ammonium hydroxide. The MeOH was stripped off and the mixture was extracted with ether. These extracts were combined, washed with water, dilute KHSO$_4$, then dried and evaporated to give 2.36 g of a yellow glass which crystallized from 50 mL of pentane on standing overnight. The yellow-white powder obtained was recrystallized from ether-hexane and furnished the title compound (0.41 g) as white, hairy needles, mp 134–136° C., Rf (ether): single spot, 0.6. By chromatography of the mother liquors and crystallization of the appropriate fractions, an additional 0.22 g of product, mp 138–139° C., was obtained.

Anal: Calcd. for C$_{19}$H$_{31}$NO$_4$ (337.45): C, 67.62; H, 9.26; N, 4.15. Found: C, 67.51; H, 9.43; N, 4.24.

Step 3

(2S,3R4S)-N-[(tert-Butyloxy)carbonyl]-2-amino-1-cyclohexyl-3 4-dihydroxy-6-methylheptane The diol of Step 2, 0.27 g, was reduced in MeOH with 60 psi H$_2$ at 60° C. in 3 hrs using 5% Rh/C catalyst. After filtering, the solvent was stripped off and the white crystals were recrystallized from $CH_2Cl_2$-hexane to furnish tiny needles of the title compound, 0.19 g, mp 126–128° C.; further recrystallization gave mp 128.5–129.5° C. Rf (ether): single spot, 0.8.

Anal: Calcd. for $C_{19}H_{37}NO_4$ (343.50): C, 66.43; H, 10.86, N, 4.08. Found: C, 66.43; H, 11.01; N, 4.03.

Step 4

(2S,3R,4S) 2-amino-1-cyclohexyl-3,4-dihydroxy-6-methylheptane

The title compound of Step 3 (10 g) was dissolved 6.9N HCl in dioxane (300 mL). The mixture was stirred for 30 minutes at room temperature. The solvent was removed in vacuo and to the residue was added 5% aqueous sodium hydroxide (30 mL) until a pH of 14 was obtained. This mixture was extracted with ether and the ether extract was washed with water and brine, then the solvent was evaporated to give the title compound (7.3 g, 100% yield). 300 MHz $^1$H NMR: consistent with proposed structure.

Anal. calcd for $C_{14}H_{29}NO_2$: C, 69.07; H, 12.01; N, 5.78. Found: C, 69.19; H, 12.34; N, 5.78.

Step 5

D,L Boc-C-propargylglycine

D,L C-propargylglycine (10 g) was suspended in tetrahydrofuran (30 mL). Water (30 mL), potassium carbonate (36.7 g), and di-tert-butyl-dicarbonate (21.9 g) were added. Additional water was added to produce a solution which was stirred for 12 hours at room temperature. The organic solvent was then evaporated and the aqueous solution was washed with ether, then acidified to pH 3 with 1N aqueous citric acid. The solution was extracted with methylene chloride and the solvent evaporated to give the title compound (18.9 g, 97% yield), used without further purification.

Step 6

N-[1S,1R*-(cyclohexylmethyl)-2S*,3R*-dihydroxy-5-methylhexyl]-2-[[(1,1-dimethylethoxy)carbonyl]amino]-4-pentynamide D,L Boc-C-propargylglycine (1.2 g) was dissolved in methylene chloride (5 mL) and N-methyl piperidine (0.57 g) was added. The mixture was cooled to zero degrees centigrade and isobutyl chloroformate (0.78 g) was added. The mixture was stirred for 10 minutes whereupon the title compound of Step 4 (1.4 g) in methylene chloride (5 mL) was added and this mixture stirred for 15 minutes at 0° C. and 4° C. for 12 hours. The reaction mixture was washed successively with 1N citric acid, saturated sodium hydrogen carbonate, waster and brine. The organic layer was dried over magnesium sulfate and evaporated to dryness. 300 MHz $^1$H NMR: consistent with proposed structure.

Step 7

2R*-amino-N-[1S,1R*-(cyclohexylmethyl)-2S*,3R*-dihydroxy-5-methylhexyl]-4-pentynamide The title compound of Step 6 (a 1:1 mixture of diastereomers) (0.76 g) was dissolved in a mixture of trifluoroacetic acid (4.9 mL) and methylene chloride (4.9 mL), and stirred for 30 minutes at room temperature. The solvent was then evaporated and the residue taken up in ethyl acetate. The organic layer was washed with saturated sodium hydrogen carbonate, water and brine, then dried over magnesium sulfate and evaporated. The residue was chromatographed on silica gel, eluting with ethanol-chloroform-ammonium hydroxide (15:85:0.5). The faster running of the two diastereomers was collected and evaporated to give the pure title compound (0.2 g, 34% yield). 300 MHz $^1$H NMR: consistent with proposed structure.

Anal. calcd for $C_{19}H_{34}N_2O_3$: C, 67.4; H, 10.12; N, 8.31. Found: C, 66.6; H, 10.05; N, 8.02.

Step 8

2R-Benzyl butanedioic acid, 1-benzyl ester, dicyclohexylammonium salt

To a slurry of 4-(4-methoxybenzyl)itaconate (prepared by the method of Talley in U.S. Pat. No. # 4,939,288) (50 g) in toluene (250 mL) was added 1,8-diazabicyclo[5.4.0]undec-7-ene (DBU, 30.4 g) in one portion. Then a solution of benzyl bromide (34.2 g) in toluene (50 mL) was added dropwise over 0.5 hour. The reaction was stirred for 0.5 hour at room temperature and then poured into a separatory funnel. The mixture was washed with 3N HCl, aqueous sodium bicarbonate, brine and dried over magnesium sulfate. The solvent was evaporated to give a clear mobile liquid (68 g). Chromatography on silica gel, eluting with from 100% hexane to 25% ethyl acetate gave pure 1-(benzyl)-4-(4-methoxybenzyl) itaconate (55 g, 81% yield). A large Fisher Porter bottle was charged with this itaconate (41 g), triethylamine (36 g), palladium acetate (380mg), tri-o-tolylphosphine (1.04 g) and iodobenzene (24.7 g). The bottle was sealed and flushed with nitrogen and placed in an oil bath and heated for 70 minutes. The residue was chromatographed on silica gel, eluting with 100% hexanes until the less polar impurities were removed. Eluting with 10% ethyl acetate in hexane gave the pure phenyl itaconate. This compound (23.8 g) was mixed with toluene (200 mL) and the resulting solution treated with trifluoroacetic acid (30 mL). The solution was stirred at room temperature for 1.5 hour and then evaporated. The residue was taken up in ether (150 mL) and treated with dicyclohexylamine (10.4 g) and stirred at 0° C. whereupon the salt precipitated. This was isolated by filtration and washed with hexane and dried to give pure 1-benzyl 2-benzylidene succinoate dicyclohexylammonium salt (21.24 g, 78% yield). This benzylidene compound (20 g) was place in a Fisher-Porter bottle and also added were degassed methanol (200 mL) and rhodium (R,R)DiPAMP (600 mg) catalyst. The bottle was sealed and flushed with nitrogen then hydrogen. The reaction was hydrogenated at 40 psig for 15 hours at room temperature. The contents were then poured into a round bottom flask (500 mL) and the solvent evaporated to give a dark solid. The residue was taken up in boiling isooctane and allowed to stand, with some title compound crystallizing (7.34 g). The non-dissolved residue was taken up in boiling dimethoxyethane. This solution was allowed to cool for 12 hours, whereupon crystals of the title compound formed (6.05 g). Combining the two crops gave 13.39 g, 66% yield, mp 122–125° C. 300 MHz $^1$H NMR: consistent with proposed structure.

Step 9

2R-Benzyl butanedioic acid, 1-benzyl ester

The title compound of Step 8 (9.3 g) was suspended in a mixture of water (84 mL) and methanol (8.5 mL). Solid sodium bisulfate (6.12) was added and the mixture stirred for 5 minutes. The mixture was extracted with methylene chloride and the combined extracts were dried over magnesium sulfate and evaporated to dryness. The residue was chromatographed on silica gel, eluting with methanol-chloroform-acetic acid (5:95:0.5), to give the pure title compound (4.3 g, 74% yield).

Step 10

Benzyl αR-[2-[[2-(dimethylamino)ethyl] methylamino]-2-oxoethyl]benzene propanoate The title compound of Step 9 (4.3 g) was dissolved in methylene chloride (200 mL) and N-methyl piperidine (1.86 g) was added. The mixture was cooled to 0° C. and isobutylchloroformate (1.97 g) was added. The mixture was stirred for 10 minutes whereupon N,N,N'-trimethylethylene diamine (2.23 g) in methylene chloride (10 mL) was added. This mixture was stirred at 4° C. for 3 hours, then washed with 1N citric acid, saturated aqueous sodium bicarbonate, water and brine. The solvent was evaporated to give the title compound (4.7 g, 85% yield). 300 MHz $^1$H NMR: consistent with proposed structure.

Step 11

αR-2-[[2-(dimethylamino)ethyl]methylamino]-2-oxoethyl]benzene propanoic acid

The title compound of Step 10 (4.6 g) was dissolved in ethanol (50 mL) and hydrogenated over 4% Pd—C at 5 psi at room temperature for 17 hours. The ethanol was evaporated to give the title compound (3 g, 71% yield). 300 MHz $^1$H NMR: consistent with proposed structure.

Step 12

O-(N-(dimethylaminoethyl)-N-methyl-aminocarbonyl)-3-L -phenyllactic acid

Benzyl L-3-phenyllactate (14.28 g) was dissolved in tetrahydrofuran (357 mL) and to this was added carbonyl diimidazole (9.78 g) and the mixture was stirred at room temperature for 4 hours. N,N,N'-trimethylethylene diamine (6.8 g) was added and the mixture stirred for 8 hours. The solvent was evaporated and the residue taken up in ether and washed with water, dried over magnesium sulfate and evaporated to give a yellow oil (13 g, 61% yield); 300 MHz $^1$H NMR consistent with proposed structure. This ester was hydrogenated over 4% Pd—C @ 5 psi and room temperature for 3.5 hours in tetrahydrofuran. The title compound was obtained as a white solid (10 g) and recrystallized from methanol.

Anal. calcd for $C_{15}H_{22}N_2O_4+H_2O$: C, 57.68; H, 7.75; N, 8.98. Found: C, 57.60; H, 7.82; N, 8.94.

Step 13

2R*-amino-N-[1S,1R*-(cyclohexylmethyl)-2S*3R*-dihydroxy-5-methylhexyl]-4-pentynamide The title compound of Step 6 (a 1:1 mixture of diastereomers) (2.3 g) was dissolved in a mixture of trifluoroacetic acid (14 mL) and methylene chloride (14 mL), and stirred for 30 minutes at room temperature. The solvent was then evaporated and the residue taken up in ethyl acetate. The organic layer was washed with saturated sodium hydrogen carbonate, water and brine, then dried over magnesium sulfate and evaporated to give the title compound as a mixture of diastereomers (1.8 g, 100% yield). 300 MHz $^1$H NMR: consistent with proposed structure.

The following working Examples are provided to illustrate synthesis of Compounds 1–34 of the present invention and are not intended to limit the scope thereof. Those skilled in the art will readily understand that known variations of the conditions and processes of the following preparative procedures can be used to prepare the compounds of the Examples. All temperatures expressed are in degrees Centigrade.

EXAMPLE 1

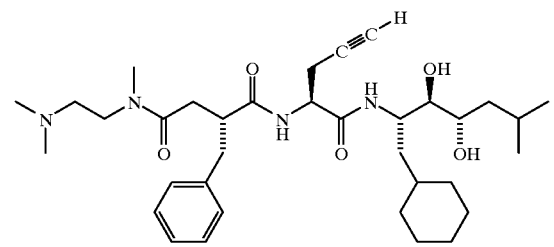

N1-[1R*-[[[1S,1R*-(cyclohexylmethyl)-2S*,3R*-dihydroxy-5-methylhexyl]amino]carbonyl]-3-butynyl]-N4-[2-(dimethylamino)ethyl]-N4-methyl-2S*-(phenylmethyl)butanediamide The title compound of Step 11 (110 mg, 0.37 mmol) was dissolved at room temperature in a mixture of dimethylformamide (10 mL) and pyridine (132 μL) and to this solution was added di-(N-succinimidyl)carbonate (85 mg, 0.33 mmol) and dimethylaminopyridine (4 mg). The mixture was stirred for 3 hours, whereupon the title amine of Step 7 (103 mg, 0.30 mmol) was added, followed by diisopropyl ethylamine (58 μL). This mixture was allowed to stir for 12 hours. The solvent was then evaporated and the residue dissolved in ethyl acetate (10 mL). This mixture was washed successively with water and brine, then dried over sodium sulfate and the solvent evaporated to give crude product (170 mg). The residue was purified by chromatography on silica gel, eluting with chloroform-ethanol-ammonium hydroxide (84:15:1) to afford the pure title compound as a white powder (130 mg, 68% yield) $^1$H NMR: 300 MHz spectrum consistent with proposed structure.

Anal. calcd for $C_{35}H_{56}N_4O_5+0.4 H_2O$: C, 67.80; H, 9.23; N, 9.04. Found, C, 67.80; H, 9.13; N, 9.02.

EXAMPLE 2

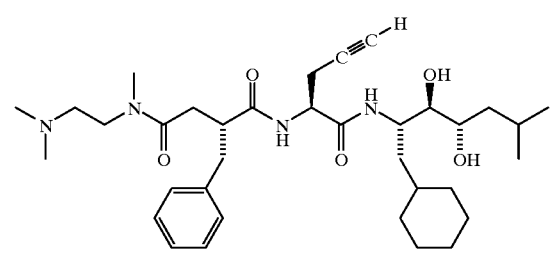

[1R*-[[[1R*-[[[1S,1R*-(cyclohexylmethyl)-2S*, 3R*-dihydroxy-5-methylhexyl]amino]carbonyl]-3-butynyl]amino]carbonyl]-2-phenylethyl)[2-(dimethylamino)ethyl]methylcarbamate The title acid of Step 12 (220 mg, 0.75 mmol) was coupled to the title amine of Step 7 (253 mg, 0.75 mmol)

19 using the procedure described for the preparation of Example 3. The crude product was purified by flash chromatography on silica gel, eluting with chloroform-ethanol-ammonium hydroxide (84:15:1), to give pure title compound (280 mg, 61% yield). $^1$H NMR: 300 MHz spectrum consistent with proposed structure.

Anal. calcd for $C_{34}H_{54}N_4O_6 + 1.5H_2O$: C, 63.62; H, 8.95; N, 8.73. Found: C, 63.89; H, 8.86; N, 8.28.

EXAMPLE 3

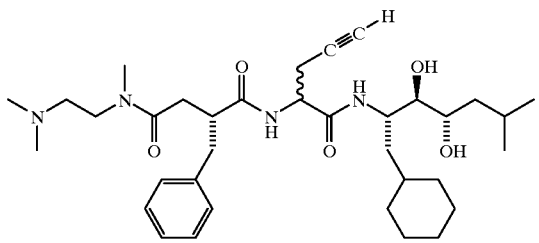

20

[1R*-[[[1-[[[1S,1R*-(cyclohexylmethyl)-2S*,3R*-dihydroxy-5-methylhexyl]amino]carbonyl]-3-butynyl]amino]carbonyl]-2-phenylethyl][2-(dimethylamino)ethyl]methylcarbamate To a solution of the title compound of Step 12 (128 mg) in methylene chloride (cooled to 0° C.) was added N-methylpiperidine (43 mg), followed by isobutylchloroformate (59 mg). After 5 minutes of stirring, a solution of the title amine of Step 13 (146 mg) in methylene chloride was added and the resulting mixture stirred for 4 hours. The solution was diluted with additional methylene chloride, then washed successively with aqueous dilute citric acid, water, aqueous potassium bicarbonate, dried over magnesioum sulfate and the solvent evaporated to dryness to give the title compound (268 mg, 100% yield). 300 MHz $^1$H NMR: consistent with proposed structure.

Anal. calcd for $C_{34}H_{54}N_4O_6$: C, 66.42; H, 8.85; N, 9.11. Found: C, 65.61; H, 8.91; N, 8.20.

Compounds #4–34, as shown in Table I below, may be synthesized by reference to the foregoing specific and general procedures for preparing compounds of Formula I.

TABLE I

| Example Compound No. | Structure |
|---|---|
| 4 | 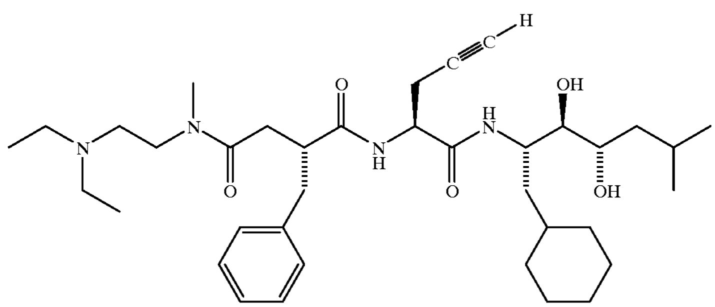 |
| 5 | 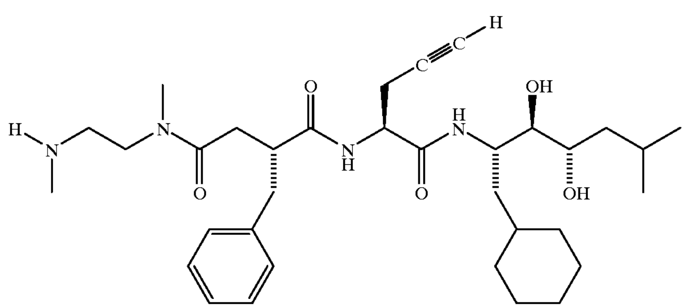 |
| 6 | 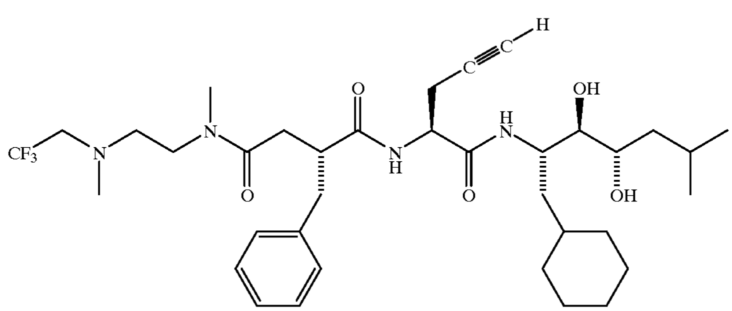 |

TABLE I-continued
| Example Compound No. | Structure |
|---|---|
| 7 | 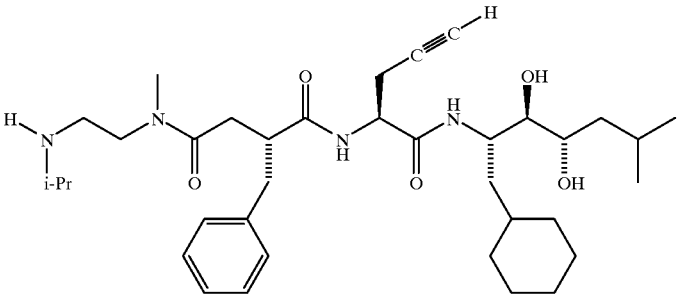 |
| 8 | 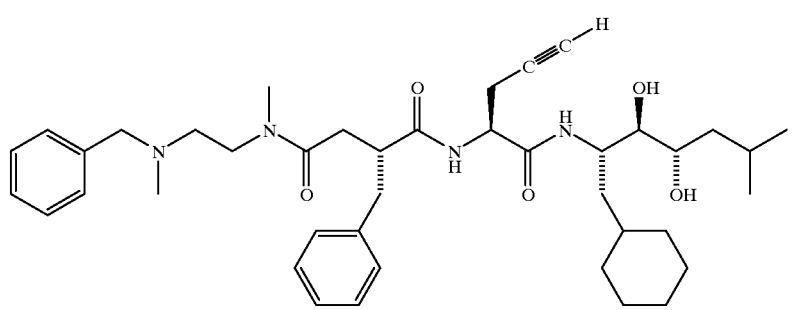 |
| 9 | 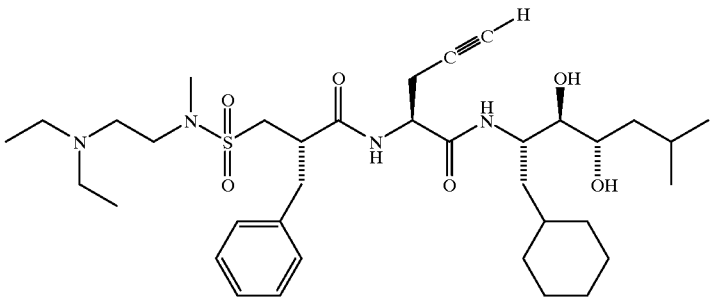 |
| 10 | 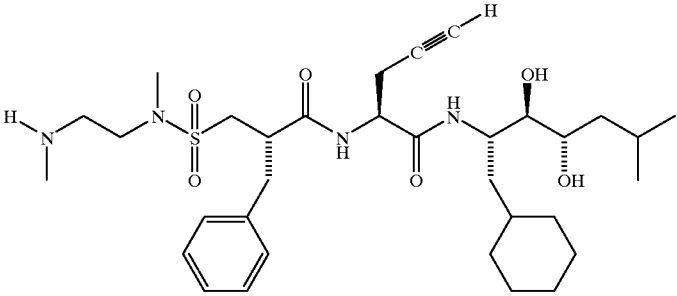 |

TABLE I-continued
| Example Compound No. | Structure |
|---|---|
| 11 | 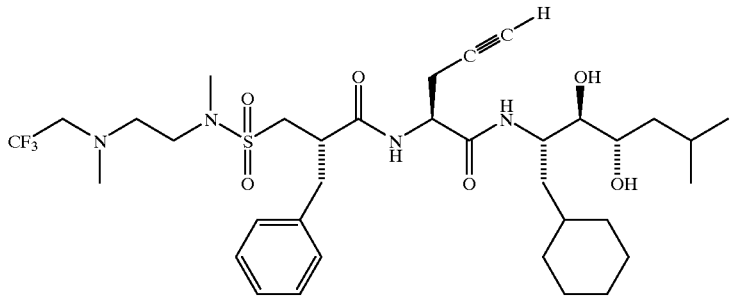 |
| 12 | 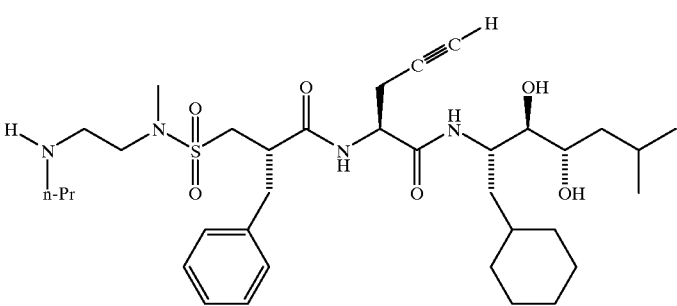 |
| 13 | 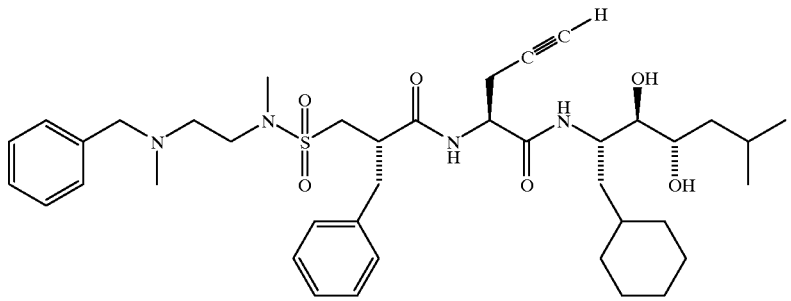 |
| 14 | 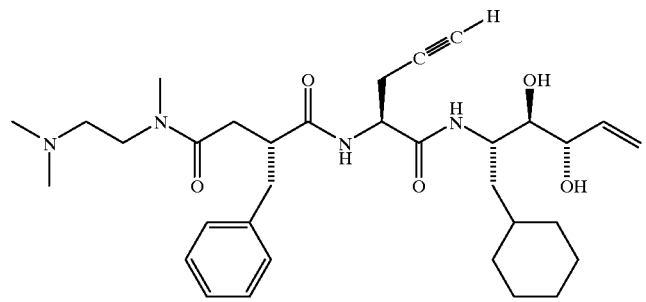 |

TABLE I-continued

| Example Compound No. | Structure |
|---|---|
| 15 | 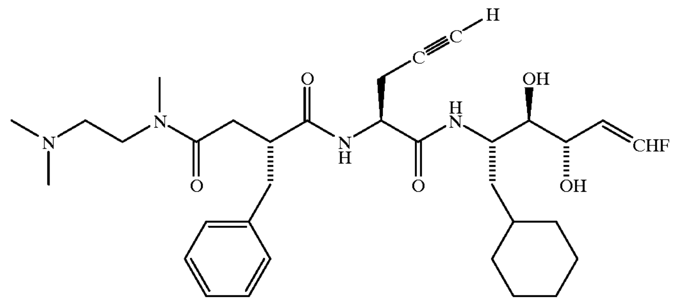 |
| 16 | 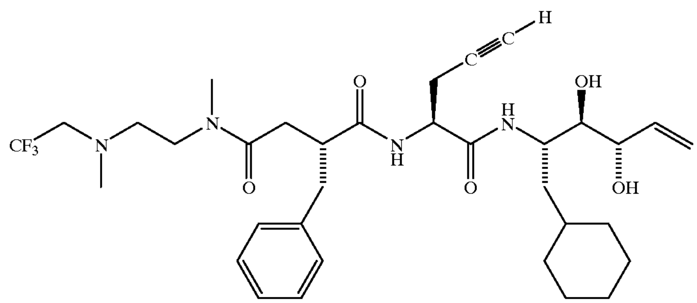 |
| 17 | 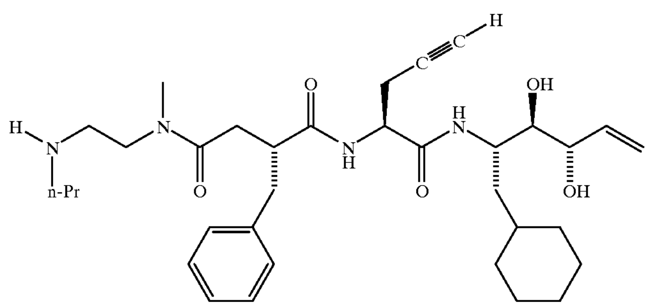 |
| 18 | 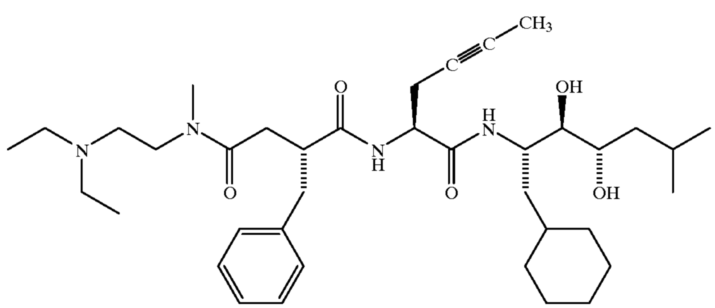 |

TABLE I-continued

| Example Compound No. | Structure |
|---|---|
| 19 | 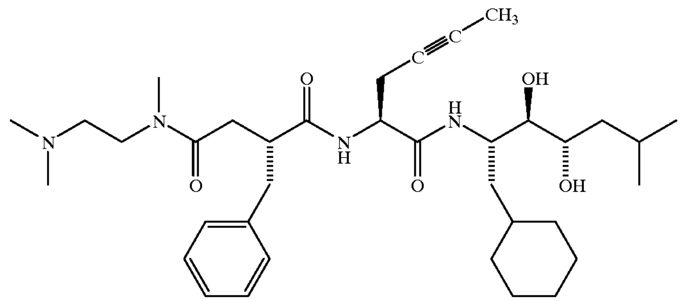 |
| 20 | 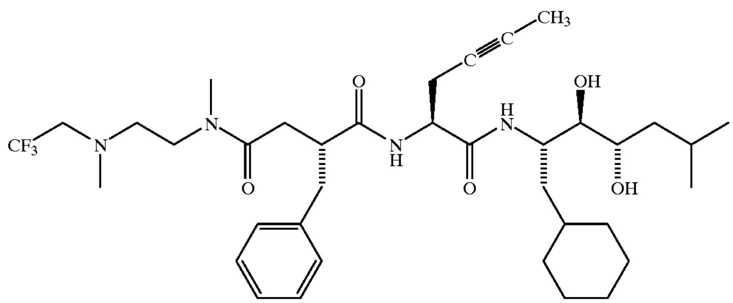 |
| 21 | 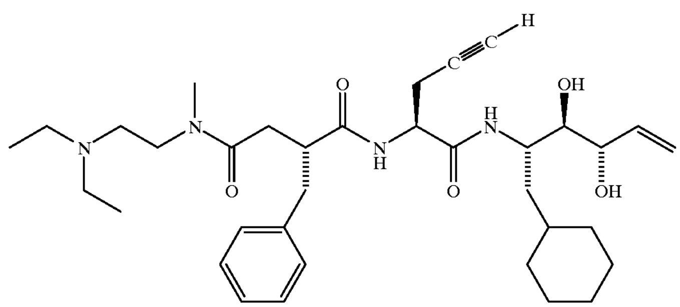 |
| 22 | 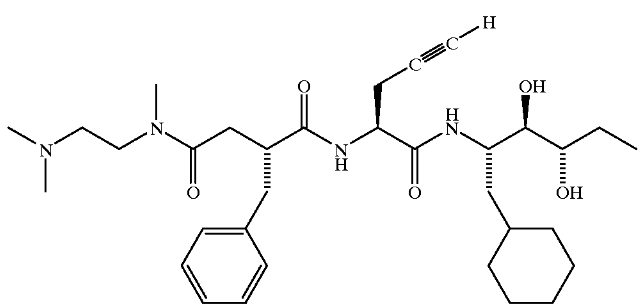 |

TABLE I-continued
| Example Compound No. | Structure |
|---|---|
| 23 | 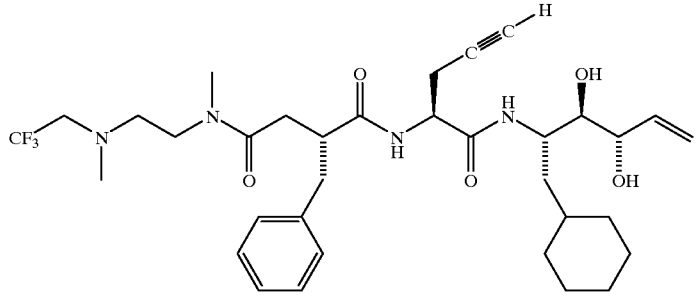 |
| 24 | 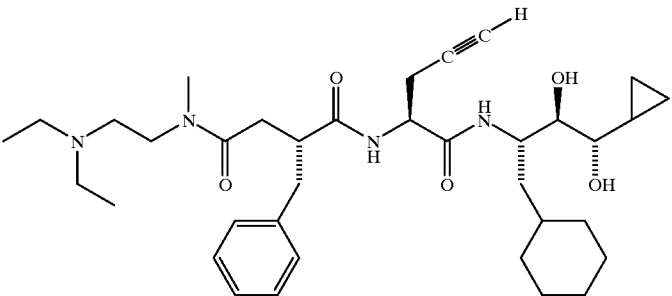 |
| 25 | 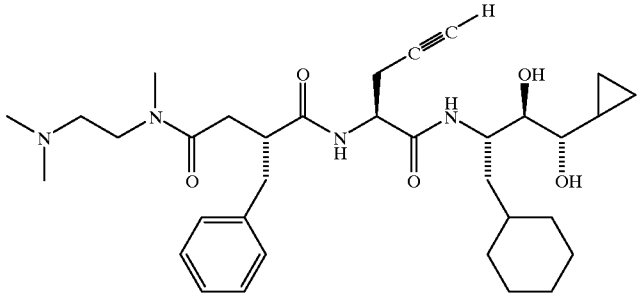 |
| 26 | 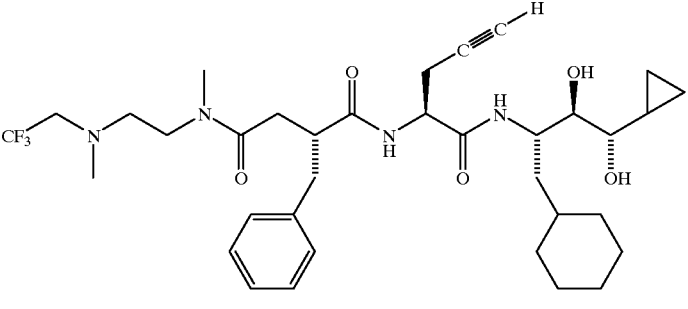 |

TABLE I-continued

| Example Compound No. | Structure |
|---|---|
| 27 | 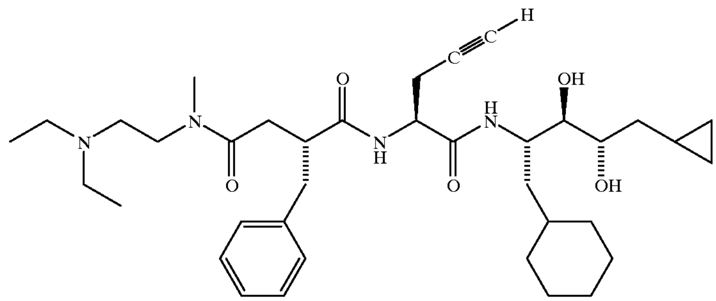 |
| 28 | 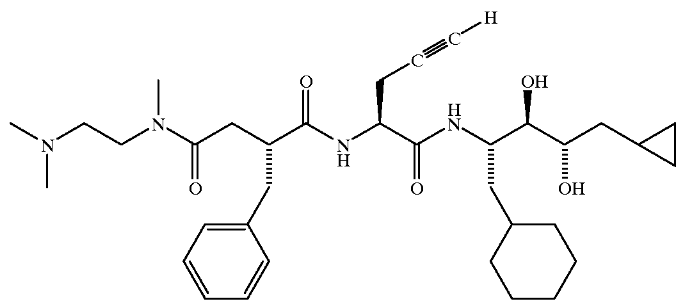 |
| 29 | 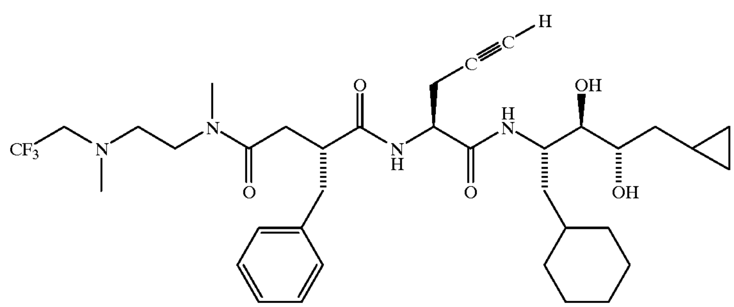 |
| 30 | 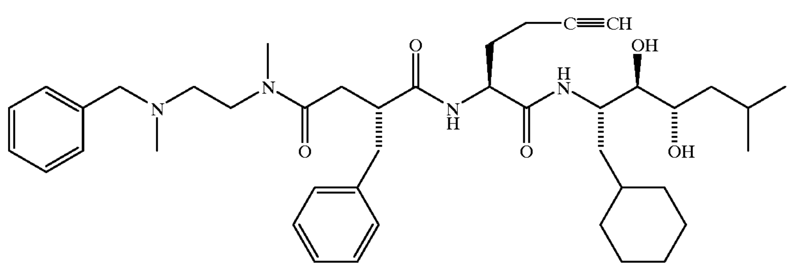 |
| 31 | 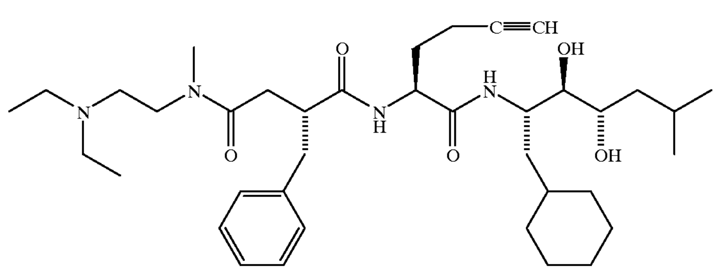 |

TABLE I-continued

| Example Compound No. | Structure |
|---|---|
| 32 | (structure depicted) |
| 33 | (structure depicted) |
| 34 | (structure depicted) |

Biological Evaluation

Human Renin Inhibition in vitro

Compounds of Formula I were evaluated as inhibitors of human renin in an in vitro assay, as follows: This human renin inhibition test has been previously described in detail [Papaioannou et al., *Clinical and Experimental Hypertension*, A7(9), 1243–1257 (1985)]. Human renin was obtained from the National Institute for Biological Standards, London. An incubation mixture was prepared containing the following components: in a total volume of 0.25 mL: 100 mM Tris-acetate buffer at pH 7.4, $25 \times 10^{-6}$ Goldblatt units of renin, 0.05 mL of plasma from human volunteers taking oral contraceptives, 6.0 mM Na-EDTA, 2.4 mM phenylmethyl sulfonyl fluoride, 1.5 mM 8-hydroxyquinoline, 0.4 mg/mL bovine serum albumin (BSA), and 0.024 mg/mL neomycin sulfate. This mixture was incubated for two hours at 37° C. in the presence or absence of renin inhibitors. The produced angiotensin I was determined by radioimmunoassay (New England Nuclear kit). Test compounds to be assayed were dissolved in DMSO and diluted with 100 mM Tris-acetate buffer at pH 7.4 containing 0.5% BSA to the appropriate concentration. The final concentration of organic solvent in the reaction mixture was less than 1%. Control incubations at 37° C. were used to correct for effects of organic solvent on renin activity.

The in vitro enzymatic conversion of angiotensinogen to angiotensin I was inhibited by test compounds of the invention as indicated in Table II, below:

TABLE II

Human Renin in vitro Inhibition Data

| Compound Example # | $IC_{50}$ Human Renin (nM) |
|---|---|
| Example 1 | 1 |
| Example 2 | 4 |
| Example 3 | 3 |
| Example 4 | 1 |

Marmoset Plasma Renin Activity (PRA) Reduction on Oral Administration

The oral activity of renin inhibitor compounds was determined in vivo in Marmoset monkeys using the following procedure. Common Marmoset monkeys (Callithrix jacchus, Charles River, both sexes, body weight 300–400 g) were placed on a modified high-protein low-sodium diet (Purina, St. Louis, Mo.) for 1 week. About 24 hours prior to the administration of test compound, Lasix (5 mg/kg, im) was given. On the day of the test, the animal was anesthetized with isoflurane, body weight recorded, and a baseline blood sample taken. Then, test compound was given intragastrically and blood samples were taken in K-EDTA for plasma renin activity at appropriate time intervals. The PRA was determined by using the protocol outlined below.

Results are shown below in Table III. Results are expressed in terms of PRA at various time intervals both before and after compound administrations ("Pre" means pretreatment levels before compound administrations). Also included is percent inhibition (% INH from pretreatment levels).

Plasma Renin Activity Assay
I. Angiotensin I Generation

| Plasma Sample | 200 ul |
|---|---|
| PMSF 5% | 1 ul |
| Neomycin 10% | 3 ul |
| 8-HQ 0.5M | 3 ul |
| TES 0.5M, pH 7.4 | 20 ul |

25 ml of the above reaction mixtures, in duplicate, were incubated at 37° C. or 0° C. for 2 hours.

II. Determination of Angiotensin I Concentrations

Angiotensin I (AI) concentrations were determined by radioimmunoassays with a commercial kit from NEN Co.

III. Calculation of Plasma Renin Activity

PRA (ng AI/ml/hr)=(AI at 37°−AI at 0°)/2 hr.

Abbreviations Used:

| PMSF | Phenylmethylsulonyfluoride |
|---|---|
| 8-HQ | 8-Hydroxyquinoline |
| BSA | Bovine Serum Albumin |
| TES | N-tris[Hydroxymethyl]methyl-2-aminoethane Sulfonic Acid |
| EDTA | Ethylenediamine Tetraacetic Acid |

TABLE III

| | | PRA (ngAI/ml/hr) | % INH | MEAN % INH |
|---|---|---|---|---|
| Effect of Oral Administration of Example 1 Compound on Marmoset PRA (0.1 MPK, IG) | | | | |
| Monkey SC53315 | | | | |
| A | Pre* | 90.1 | | |
| | 60 | 4 | 95.6 | 88.7 ± 6 |
| | 120 | 5.2 | 94.2 | 85.6 ± 7 |
| | 240 | 9.2 | 89.8 | 67.5 ± 13 |
| B | Pre* | 45.8 | | |
| | 60 | 2.8 | 93.8 | |
| | 120 | 4.1 | 91.1 | |
| | 240 | 14.8 | 67.8 | |
| C | Pre* | 70.2 | | |
| | 60 | 16.4 | 76.6 | |
| | 120 | 20 | 71.5 | |
| | 240 | 38.7 | 45 | |
| Effect of Oral Administration of Example 2 Compound on Marmoset PRA (0.1 MPK, IG) | | | | |
| Monkey SC53592 | | | | |
| A | Pre* | 118.8 | | |
| | 60 | 33.9 | 71.5 | 81.1 ± 6 |
| | 120 | 41.8 | 64.8 | 76.6 ± 6 |
| | 240 | 49.7 | 58.2 | 57.7 ± 0 |
| B | Pre* | 67.5 | | |
| | 60 | 12.7 | 81.2 | |
| | 120 | 14.4 | 78.7 | |
| | 240 | 28.5 | 57.7 | |
| C | Pre* | 42.2 | | |
| | 60 | 3.9 | 90.7 | |
| | 120 | 5.7 | 86.4 | |
| | 240 | 18.1 | 57.2 | |
| Effect of Oral Administration of Example 3 Compound on Marmoset PRA (0.1 MPK, IG) | | | | |
| Monkey SC53174 | | | | |
| A | Pre* | 76 | | |
| | 60 | 29.8 | 60.7 | 62.5 ± 2 |
| | 120 | 40.3 | 46.9 | 54.2 ± 4 |
| | 240 | 39.5 | 48 | 56.2 ± 5 |
| B | Pre* | 83.7 | | |
| | 60 | 27.8 | 66.7 | |
| | 120 | 33.2 | 60.3 | |
| | 240 | 36.1 | 56.8 | |
| C | Pre* | 105.5 | | |
| | 60 | 42.1 | 60.1 | |
| | 120 | 47.1 | 55.3 | |
| | 240 | 38.1 | 63.9 | |
| Effect of Oral Administration of Example 3 Compound on Marmoset PRA 10 MPK, IG) | | | | |
| Monkey A | Pre* | 185.4 | | |
| | 60 | 0 | 100 | 100 ± 0 |
| | 120 | 0 | 100 | 100 ± 0 |
| | 240 | 0 | 100 | 100 ± 0 |
| B | Pre* | 76.1 | | |
| | 60 | 0 | 100 | |
| | 120 | 0 | 100 | |
| | 240 | 0 | 100 | |
| C | Pre* | 70.5 | | |
| | 60 | 0 | 100 | |
| | 120 | 0 | 100 | |
| | 240 | 0 | 100 | |

*Time in minutes from dosing

Determination of Oral Bioavailability

The bioavailability in marmosets and dogs was determined by sampling the blood via the femoral vein at various time points after administering the renin inhibitor compounds of the invention in polyethylene glycol 400 at an intragastric dose of 10 mg/kg or at an intravenous dose of 1 mg/kg. Compound concentration in plasma was determined using the bioassay technique described below. The percent bioavailability was calculated by dividing the area under the concentration-vs.-time curve obtained from the intragastric experiment by the area under the concentration-vs.-time curve obtained from the intravenous experiment (adjusting for different doses), and multiplying the result by 100%. The bioavailability of Example 1 compound is 27% in marmosets and 33% in dogs.

Renin inhibitor plasma concentrations were determined by a bioassay. The plasma samples were extracted with acetonitrile and the extract was evaporated to dryness under nitrogen. Residue was dissolved in 4% bovine serum albumin containing 0.9% NaCl and 5% EDTA. The dissolved residue (0.1 ml) was incubated with a reaction mixture containing human plasma (0.12 ml), 5% phenylmethysulfonylfluoride (1.2 ul), 10% neomycin (2.4 ul), 0.5 M TES buffer (pH 7.4, 24 ul), and 0.6 mU/ml recombinant human renin (1000 U/mg, 50 ul) at 37° C. for 90 minutes. The renin activity was determined by a standard angiotensin I radioimmunoassay (New England Nuclear Corp.). The amount of test compound in the plasma was determined by comparing the extent of inhibition of renin activity with that produced by a known amount of test compound added to plasma and analyzed above.

EXAMPLE 1

Compound Oral Bioavailability Studies in Dogs

| | Estimated Plasma Concentration (ng/ml) | | | |
|---|---|---|---|---|
| | Animal Number | | | |
| Time | #1 | #2 | #3 | Mean ± SE |
| IG at 10 mg/kg: | | | | |
| 15 min | 105.7 | <2.0 | 265.6 | 127.7 ± 77.2 |
| 30 min | 495.9 | 330.4 | 864.7 | 563.7 ± 157.9 |
| 1 hr | 678.2 | 859.6 | 859.6 | 799.1 ± 60.5 |
| 2 hr | 599.2 | 352.7 | 554.5 | 502.1 ± 75.8 |
| 4 hr | 123.4 | 68.8 | 130.3 | 110.5 ± 20.9 |
| 6 hr | 66.9 | 47.1 | 72.4 | 62.1 ± 7.7 |
| 8 hr | 33.5 | 25.4 | 45.4 | 34.8 ± 5.8 |
| 24 hr | 6.2 | 8.4 | 8.0 | 7.5 ± 0.7 |
| IV at 1 mg/kg: | | | | |
| 2 min | 2417.7 | 3284.4 | 2982.7 | 2894.9 ± 254.0 |
| 5 min | 613.1 | 680.9 | 521.1 | 605.0 ± 46.3 |
| 10 min | 299.0 | 307.1 | 218.0 | 274.7 ± 28.4 |
| 15 min | 218.0 | 144.4 | 146.9 | 169.8 ± 24.1 |
| 30 min | 144.7 | 102.8 | 122.5 | 123.3 ± 12.1 |
| 1 hr | 70.4 | 67.6 | 50.0 | 62.7 ± 6.4 |
| 2 hr | 48.8 | 56.0 | 69.8 | 58.2 ± 6.2 |
| 4 hr | 18.6 | 23.5 | 23.5 | 21.9 ± 1.6 |
| 6 hr | 10.1 | 10.2 | 13.5 | 11.3 ± 1.1 |

-continued

| | Estimated Plasma Concentration (ng/ml) | | | |
|---|---|---|---|---|
| | Animal Number | | | |
| Time | #1 | #2 | #3 | Mean ± SE |
| 8 hr | 6.4 | 4.9 | 6.1 | 5.8 ± 0.5 |
| 24 hr | 2.5 | 1.5 | 1.3 | 1.8 ± 0.4 |

Summary of Example 1 Oral Bioavailability Studies in Dogs

| | Animal number | | | |
|---|---|---|---|---|
| | #1670841 | #1671430 | #KOV9 | Mean ± SE |
| t1/2 (hr) | 5.3 | 4.4 | 4.3 | 4.7 ± 0.3 |
| Vd (1/kg) | 11.5 | 8.7 | 8.3 | 9.5 ± 1.0 |
| Oral (%) Bioavail | 35.8 | 25.6 | 38.0 | 33.1 ± 3.8 |

The foregoing data show that the oral bioavailability of Example 1 Compound in dogs is 33%, with a terminal half-life of 4.7 hours and a volume of distribution of 9.5 liters/kg.

Example 1 Compound Oral Biolioavailability Studies in Maramosets

| | Plasma Concentrations (ng/ml) | | | | | | |
|---|---|---|---|---|---|---|---|
| | IG at 10 mg/kg: | | | | | | |
| | Animal number | | | | | | |
| Time | #1 | #2 | #3 | #4 | #5 | #6 | Mean ± SE |
| Test Run A | | | | | | | |
| 30 min | — | — | — | 9864 | 7258 | 9322 | |
| 1 hr | 1340 | 1989 | 1751 | — | — | — | |
| 2 hr | 1561 | 1525 | 1811 | — | — | — | |
| 3 hr | — | — | — | 7051 | 5289 | 6935 | |
| 4 hr | 742 | 1766 | 1217 | — | — | — | |
| 5 hr | 369 | 1397 | 945 | — | — | — | |
| 6 hr | — | — | — | 4914 | 3177 | 4412 | |
| 8 hr | — | — | — | 3570 | 3036 | 3800 | |

| | IG at 10 mg/kg: | | | | | | |
|---|---|---|---|---|---|---|---|
| | Animal number | | | | | | |
| Time | #224 | #226 | #227 | #228 | #229 | #230 | Mean ± SE |
| Test Run B | | | | | | | |
| 30 min | — | — | — | 1344 | 1016 | 1126 | 4988 ± 1749 |
| 1 hr | 416 | 5266 | 12300 | — | — | — | 3837 ± 1818 |
| 2 hr | 519 | 4847 | 13485 | — | — | — | 3958 ± 1997 |
| 3 hr | — | — | — | 2751 | 3640 | 1400 | 4511 ± 939 |
| 4 hr | 459 | 4502 | 11470 | — | — | — | 3359 ± 1727 |
| 5 hr | 545 | 3718 | 7783 | — | — | — | 2460 ± 1174 |
| 6 hr | — | — | — | 2859 | 2721 | 1950 | 3428 ± 457 |
| 8 hr | — | — | — | 1805 | 1566 | 1868 | 2608 ± 400 |

-continued

| | | | Plasma Concentrations (ng/ml) | | | | |
|---|---|---|---|---|---|---|---|
| | | | IV at 1 mg/kg | | | | |
| | | | Animal number | | | | |
| Time | #233 | #234 | #235 | #241 | #244 | #245 | Mean ± SE |
| Test Run C | | | | | | | |
| 2 min | 13706 | 21579 | 16641 | — | — | — | |
| 15 mi | — | — | — | 6756 | 15283 | 11628 | |
| 30 min | 5858 | 10359 | 7921 | — | — | — | |
| 1 hr | — | — | — | 3091 | 2665 | 2793 | |
| 2 hr | 795 | 2362 | 1667 | — | — | — | |
| 3 hr | — | — | — | 486 | 404 | 562 | |
| 4 hr | 608 | 1223 | 1068 | — | — | — | |
| 6 hr | — | — | — | 264 | 208 | 245 | |
| | | | IV at 1 mg/kg | | | | |
| | | | Animal number | | | | |
| Time | #233 | #234 | #235 | #237 | #239 | #240 | Mean ± SE |
| Test Run D | | | | | | | |
| 2 min | 4199 | 7875 | 5900 | — | — | — | 11650 ± 2772 |
| 15 min | — | — | — | 7239 | 2016 | 897 | 7303 ± 2248 |
| 30 min | 1954 | 2356 | 1189 | — | — | — | 4939 ± 1514 |
| 1 hr | — | — | — | 1250 | 1614 | 3149 | 2427 ± 326 |
| 2 hr | 554 | 1004 | 1055 | — | — | — | 1239 ± 271 |
| 3 hr | — | — | — | 451 | 557 | 1009 | 578 ± 90 |
| 4 hr | 153 | 587 | 506 | — | — | — | 691 ± 160 |
| 6 hr | — | — | — | 95 | 84 | 158 | 176 ± 31 |

The foregoing data show that the oral bioavailability of Example 1 Compound in Marmosets is 27%, with a terminal half-life of 1.5 hours and a volume of distribution of 0.2 liters/kg.

Renin Inhibitor Species Specificity Method

Blood was collected in a 10 ml Becton Dickinson vacutainer tube with 0.1 ml of 15% EDTA (K3) solution (15 mg) from normal animals or high renin animals; i.e., those pretreated with 5 mg/kg of Lasix® intramuscularly 2 times within a 6 hour interval 24 hours prior to bleeding. The blood was then centrifuged at 2500 RPM for 20 minutes and the plasma from the various species respectively pooled, aliquoted and stored in the freezer. The human plasma source was a male Caucasian taking a prescription of an angiotensin converting enzyme inhibitor.

The plasma renin activity assay is a modification of the human renin inhibition test in that the animal plasma is the source of both the renin substrate and the renin enzyme. In a total volume of 0.1 ml, 90 mM Tris-acetate buffer, pH 7.5, 12 mM sodium EDTA, 0.012 mg/ml neomycin sulfate, 0.9 mg/ml bovine serum albumin, 1.61 mM phenylmethyl sulfonyl fluoride, 4 mM 8-hydroxyquinoline and 0.09 ml of the animal or human plasmas were incubated for 2 hours at 37° C. in a shaking water bath or at 4° C. in an ice bath in the presence or absence of renin inhibitors. The produced angiotensin I was determined by radioimmunoassay (New England Nuclear kit).

The amount of angiotensin I generated during the 2 hours at 4° C. was usually less than 5% of that activity produced at 37° C.; however, the 4° C. background values were nevertheless subtracted from the 37° C. ones for the 100% activity values. The renin inhibitors were assayed in duplicate using 5 concentrations and the data is expressed as a percent of the 100% total renin activity.

Species Specificity of Example 1

| | % of Total Renin Activity | | | |
|---|---|---|---|---|
| Plasma Conc | Human | Marmoset Monkey | Cyno Monkey | Rat |
| 1600 nM | | | | (23–34) |
| 400 nM | | | | 76% |
| | | | | (74–80) |
| 100 nM | | | | 93% |
| | | | | (91–94) |
| 16 nM | 10% | 11% | 18% | |
| | (7–13) | (10–12) | (11–22) | |
| 4 nM | 50% | 42% | 51% | |
| | (49–51) | (38–45) | (46–55) | |
| 1 nM | 90% | 75% | 81% | |
| | (80–98) | (69–83) | (74–89) | |
| 0.25 nM | | 94% | | |
| | | (89–98) | | |

The Effect of Example 1 on Marmoset Blood Pressure Reduction on Intravenous Administration The blood pressure reducing activity of the renin inhibitor compound of Example 1 was determined in vivo in Marmoset monkeys using the following procedure. Common Marmoset monkeys (Callithrix jacchus, Charles River, both sexes, body weight ca. 400 g) were placed on a modified high protein low sodium diet (Purina, St. Louis, Mo.) for 1 week. 24 hours prior to the administration of test compound, Lasix (5 mg/kg, im) was given. On the day of the test, the animal was anesthetized with isoflurane, body weight recorded, and the left femoral artery and vein were catheterized. The animal was allowed to regain consciousness and the title compound of Example 1 (100 micrograms/kg) was administered intravenously in 0.1 mL/kg polyethylene glycol 400 at time zero. Mean arterial blood pressure (MABP) in mmHg was then recorded every ten minutes until 120 minutes.

The Effect of Example 1 on Marmoset Blood Pressure Reduction on Intravenous Administration

| Time (minutes) | MABP | S.E.M. | Statistical Significance |
| --- | --- | --- | --- |
| 0 | 118 | 6.240 | |
| 10 | 106 | 3.210 | * |
| 20 | 97 | 5.290 | |
| 30 | 93 | 5.290 | * |
| 40 | 92 | 9.290 | * |
| 50 | 90 | 9.290 | |
| 60 | 89 | 3.210 | * |
| 70 | 87 | 2.310 | * |
| 80 | 88 | 1.730 | * |
| 90 | 89 | 4.040 | * |
| 100 | 91 | 5.290 | * |
| 110 | 93 | 4.160 | |
| 120 | 94 | 3.610 | * |

*the asterisk denotes statistically significant ($p < 0.05$) differences from MABP at time zero by paired t-test ($n = 3$).

These results indicate that Example 1 compound lowers blood pressure in salt-depleted, conscious marmosets.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 400 mg of active compound per unit dosage form. A more preferred dosage will contain from about 2 mg to about 200 mg of active compound per unit dosage form. Most preferred is a dosage form containing from about 3 mg to about 100 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A therapeutic method for treating a disorder mediated by plasma renin activity, said method comprising administering to a patient a therapeutically-effective amount of a compound of Formula I:

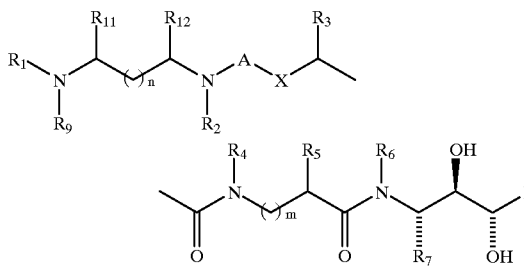
(I)

wherein A is selected from methylene, CO, SO and SO$_2$; wherein X is selected from oxygen atom, methylene and

with R$_{10}$ selected from hydrido, alkyl and benzyl; wherein each of R$_1$ and R$_9$ is a group independently selected from hydrido, alkyl, cycloalkyl, alkoxyacyl, haloalkyl, alkoxycarbonyl, benzyloxycarbonyl, loweralkanoyl, haloalkylacyl, phenyl, benzyl, naphthyl, and naphthylmethyl, any one of which groups having a substitutable position may be optionally substituted with one or more radicals selected from alkyl, alkoxy, alkenyl, alkynyl, halo, haloalkyl, cyano and phenyl, and wherein the nitrogen atom to which R$_1$ and R$_9$ are attached may be combined with oxygen to form an N-oxide; wherein R$_2$ is selected from hydrido, alkyl, dialkylaminoalkyl, alkylacylaminoalkyl, benzyl and cycloalkyl; wherein R$_3$ is selected from alkyl, cycloalkylalkyl, acylaminoalkyl, phenylalkyl, naphthylmethyl, aryl, heterocyclicalkyl and heterocycliccycloalkyl, wherein the cyclic portion of any of said phenylalkyl, naphthylmethyl, aryl, heterocyclicalkyl and heterocycliccycloalkyl groups may be substituted by one or more radicals selected from halo, hydroxy, alkoxy and alkyl; wherein each of R$_4$ and R$_6$ is independently selected from hydrido, alkyl, benzyl and cycloalkyl; wherein R$_5$ is selected from

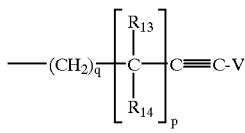

wherein V is selected from hydrido, alkyl, cycloalkyl, haloalkyl, benzyl and phenyl; wherein each of R$_{13}$ and R$_{14}$ is a radical independently selected from hydrido, alkyl, alkenyl, alkynyl, cycloalkyl, phenyl, heterocyclic, heterocyclicalkyl and heterocycliccycloalkyl; wherein R$_7$ is selected from substituted or unsubstituted alkyl, cycloalkyl, phenyl, cycloalkylalkyl and phenylalkyl, any one of which may be substituted with one or more groups selected from alkyl, hydroxy, alkoxy, halo, haloalkyl, alkenyl, alkynyl and cyano; wherein R$_8$ is selected from hydrido, alkyl, haloalkyl, alkylcycloalkyl, cycloalkyl, cycloalkylalkyl, hydroxyalkyl, alkenyl, alkylcycloalkenyl and alkoxycarbonyl; wherein each of R$_{11}$ and R$_{12}$ is independently selected from hydrido, alkyl, haloalkyl, dialkylamino and phenyl; and wherein m is zero or one; wherein n is a number selected from zero through five; wherein p is a number selected from zero through five; and wherein q is a number selected from zero through five; or a pharmaceutically-acceptable salt thereof.

2. The method of claim 1 wherein A is selected from methylene, CO, SO and SO$_2$; wherein X is selected from oxygen atom, methylene and

with R$_{10}$ selected from hydrido, alkyl and benzyl; wherein each of R$_1$ and R$_9$ is independently selected from hydrido, lower alkyl, haloalkyl, cycloalkyl, alkoxycarbonyl, benzyloxycarbonyl, loweralkanoyl, alkoxyacyl, phenyl and benzyl, and wherein the nitrogen atom to which R$_1$ and R$_9$ are attached may be combined with oxygen to form an N-oxide; wherein each of R$_2$, R$_4$ and R$_6$ is independently selected from hydrido and alkyl; wherein R$_3$ is selected from phenylalkyl, naphthylmethyl, cyclohexylalkyl, cyclopentylalkyl, heteroarylalkyl and heteroarylcycloalkyl; wherein R$_5$ is selected from

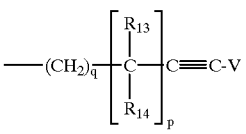

wherein V is selected from hydrido, alkyl, haloalkyl, benzyl and phenyl; wherein each of R$_{13}$ and R$_{14}$ is a radical independently selected from hydrido, alkyl, alkenyl, alkynyl, cycloalkyl, heteroaryl, heteroarylalkyl and heteroarylcycloalkyl; wherein R$_7$ is selected from substituted or unsubstituted cyclohexylmethyl and benzyl, either one of which may be substituted with one or more groups selected from alkyl, hydroxy, alkoxy, halo and haloalkyl; wherein R$_8$ is selected from hydrido, methyl, ethyl, n-propyl, n-butyl, isobutyl, cycloalkyl, cycloalkylalkyl, hydroxyalkyl, alkenyl, fluoroalkenyl and fluoroalkyl; wherein each of R$_{11}$ and R$_{12}$ is independently selected from hydrido, alkyl, dialkylamino and phenyl; wherein m is zero or one; wherein n is a number selected from zero through five; wherein p is a number selected from zero through five; and wherein q is a number selected from zero through five; or a pharmaceutically-acceptable salt thereof.

3. The method of claim 2 wherein A is selected from methylene, CO, SO and SO$_2$; wherein X is selected from oxygen atom, methylene and

with R$_{10}$ selected from hyrido, alkyl and benzyl; wherein each of R$_1$ and R$_9$ is independently selected from hydrido, alkyl, alkoxyacyl, haloalkyl, alkoxycarbonyl, benzyloxycarbonyl and benzyl, and wherein the nitrogen atom to which R$_1$ and R$_9$ are attached may be combined with oxygen to form an N-oxide; wherein each of R$_2$, R$_4$ and R$_6$ is independently selected from hydrido and alkyl; wherein R$_3$ is selected from benzyl, phenethyl, cyclohexylmethyl, phenpropyl, pyrrolidinyl, piperidinyl, pyrrolidinylmethyl, piperidinylmethyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, thiazolylcyclopropyl, imidazolecyclopropyl, thienylcyclopropyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_5$ is selected from

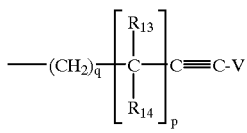

wherein V is selected from hydrido, alkyl and haloalkyl; wherein each of $R_{13}$ and $R_{14}$ is a radical independently selected from hydrido, alkyl, alkenyl, alkynyl, thiazole and thiazolemethyl; wherein $R_7$ is cyclohexylmethyl; wherein $R_8$ is selected from ethyl, n-propyl, isobutyl, cycloalkyl, cycloalkylalkyl, alkenyl, fluoroalkenyl and perfluoropropyl; wherein each of $R_{11}$ and $R_{12}$ is independently selected from hydrido, alkyl, dialkylamino and phenyl; wherein m is zero or one; wherein n is a number selected from zero through five; wherein p is a number selected from zero through five; and wherein q is a number selected from zero through five; or a pharmaceutically-acceptable salt thereof.

4. The method of claim 3 wherein A is selected from CO and $SO_2$; wherein X is selected from oxygen atom, methylene and

with $R_{10}$ selected from hydrido and methyl; wherein each of $R_1$ and $R_9$ is independently selected from hydrido, lower alkyl, alkoxyacyl, alkoxycarbonyl, benzyloxycarbonyl, haloalkyl and benzyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, phenethyl, cyclohexylmethyl, pyrrolidinyl, piperidinyl, pyrrolidinylmethyl, piperidinylmethyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, thiazolylcyclopropyl, imidazolecyclopropyl, thienylcyclopropyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein each of $R_4$ and $R_6$ is independently selected from hydrido and methyl; wherein $R_5$ is selected from

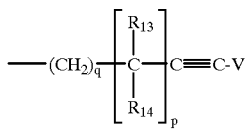

wherein V is selected from hydrido, alkyl and trifluoromethyl; wherein each of $R_{13}$ and $R_{14}$ is a radical independently selected from hydrido, alkyl and alkynyl; wherein $R_7$ is cyclohexylmethyl; wherein $R_8$ is independently selected from ethyl, n-propyl, isobutyl, cyclopropyl, cyclobutyl, cyclopentyl, cyclohexyl, cyclopropylmethyl, cyclobutylmethyl, cyclopentylmethyl, cyclopentylethyl, cyclohexylmethyl, cyclohexylethyl, allyl, vinyl and fluorovinyl; wherein each of $R_{11}$ and $R_{12}$ is independently selected from hydrido, alkyl, dialkylamino and phenyl; wherein m is zero; wherein n is a number selected from zero through five; wherein p is a number selected from zero through five; and wherein q is a number selected from zero through five; or a pharmaceutically-acceptable salt thereof.

5. The method of claim 4 wherein A is selected from CO and $SO_2$; wherein X is selected from oxygen atom and methylene; wherein each of $R_1$ and $R_9$ is independently selected from hydrido, methyl, ethyl, n-propyl, isopropyl, benzyl, β,β,β-trifluoroethyl, t-butyloxycarbonyl and methoxymethylcarbonyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, cyclohexylmethyl, phenethyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_5$ is selected from

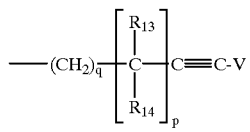

wherein V is selected from hydrido, alkyl and trifluoromethyl; wherein each of $R_{13}$ and $R_{14}$ is a radical independently selected from hydrido, methyl, ethyl, propyl and ethynyl; wherein $R_7$ is cyclohexylmethyl; wherein each of $R_4$ and $R_6$ is independently selected from hydrido and methyl; wherein $R_8$ is selected from ethyl, n-propyl, isobutyl, cyclopropyl, cyclobutyl, cyclopentyl, cyclohexyl, cyclopropylmethyl, cyclohexylmethyl, cyclohexylethyl, fluorovinyl, allyl and vinyl; wherein each of $R_{11}$ and $R_{12}$ is independently selected from hydrido, alkyl, dialkylamino and phenyl; wherein m is zero; wherein n is a number selected from zero through five; wherein p is a number selected from zero through five; and wherein q is a number selected from zero through five; or a pharmaceutically-acceptable salt thereof.

6. The method of claim 5 wherein A is selected from CO and $SO_2$; wherein X is selected from oxygen atom and methylene; wherein each of $R_1$ and $R_9$ is a group independently selected from hydrido, methyl, ethyl, n-propyl, isopropyl, benzyl, β,β,β-trifluoroethyl, t-butyloxycarbonyl and methoxymethylcarbonyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, cyclohexylmethyl, phenethyl, imidazolemethyl, pyridylmethyl and 2-pyridylethyl; wherein $R_5$ is selected from

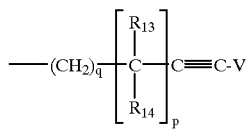

wherein V is selected from hydrido, alkyl and trifluoromethyl; wherein each of $R_{13}$ and $R_{14}$ is a radical independently selected from hydrido, methyl and ethynyl; wherein $R_7$ is cyclohexylmethyl; wherein each of $R_4$ and $R_6$ is independently selected from hydrido and methyl; wherein $R_8$ is selected from ethyl, n-propyl, isobutyl, cyclopropyl, cyclobutyl, cyclopentyl, cyclohexyl, cyclopropylmethyl, cyclohexylmethyl, cyclohexylethyl, allyl, vinyl and fluorovinyl; wherein each of $R_{11}$ and $R_{12}$ is independently selected from hydrido, alkyl and phenyl; wherein m is zero; wherein n is a number selected from zero through three; wherein p is a number selected from one through three; and wherein q is zero or one; or a pharmaceutically-acceptable salt thereof.

7. The method of claim 6 wherein said compound is selected from compounds, their tautomers, and the pharmaceutically-acceptable esters and salts thereof, of the group consisting of

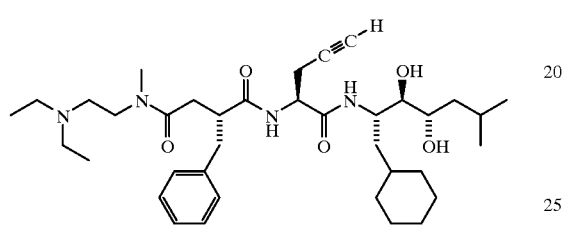

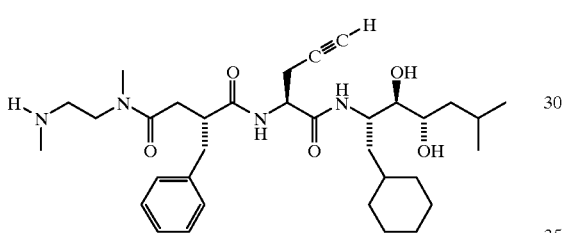

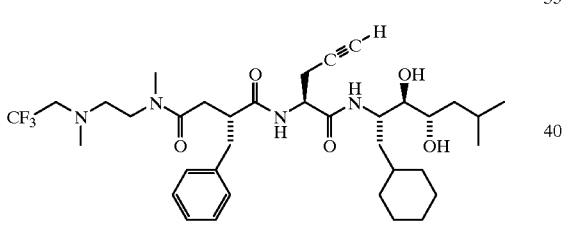

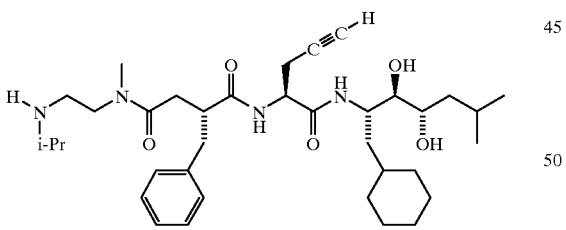

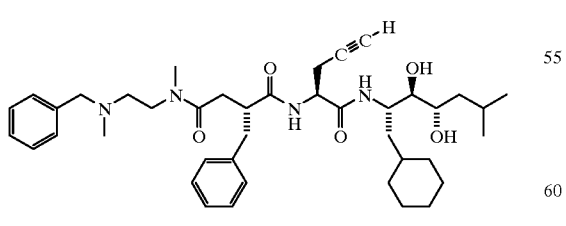

-continued

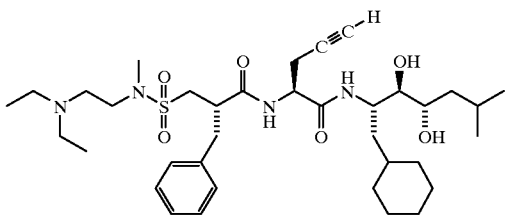

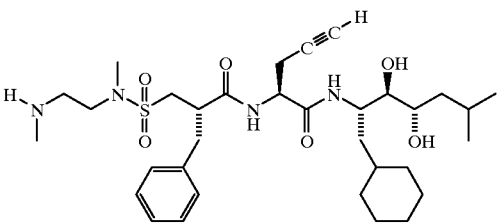

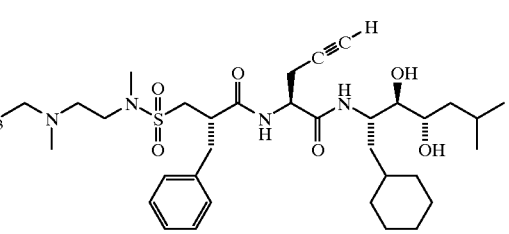

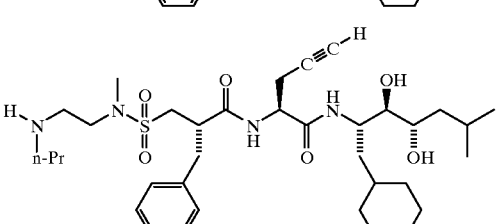

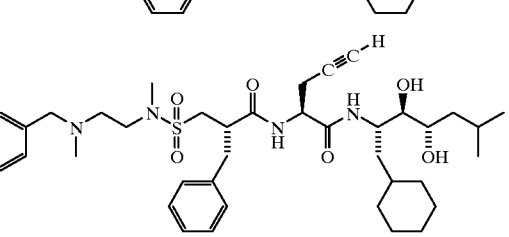

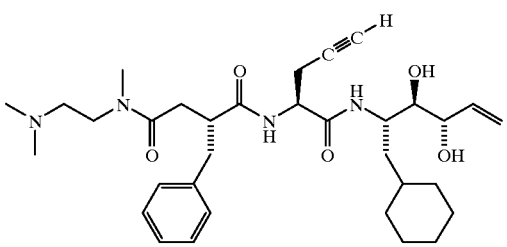

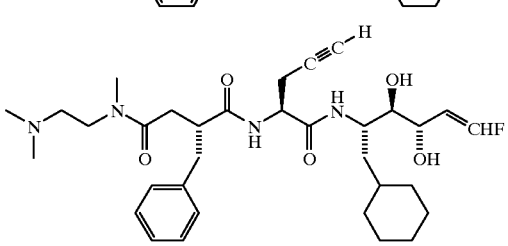

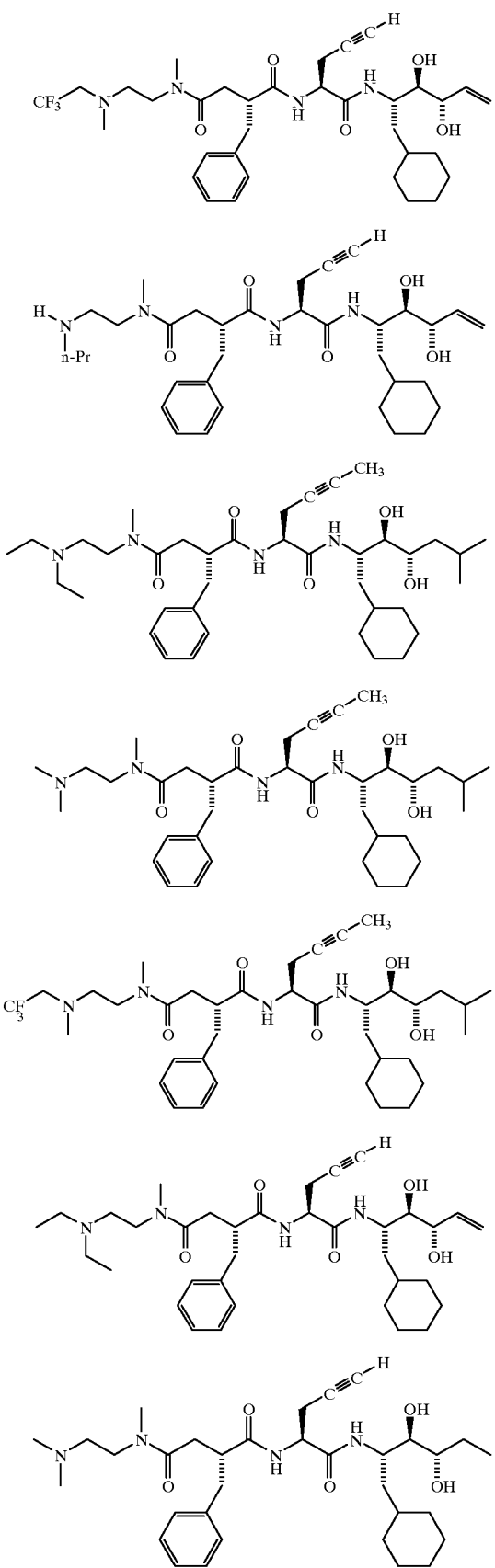
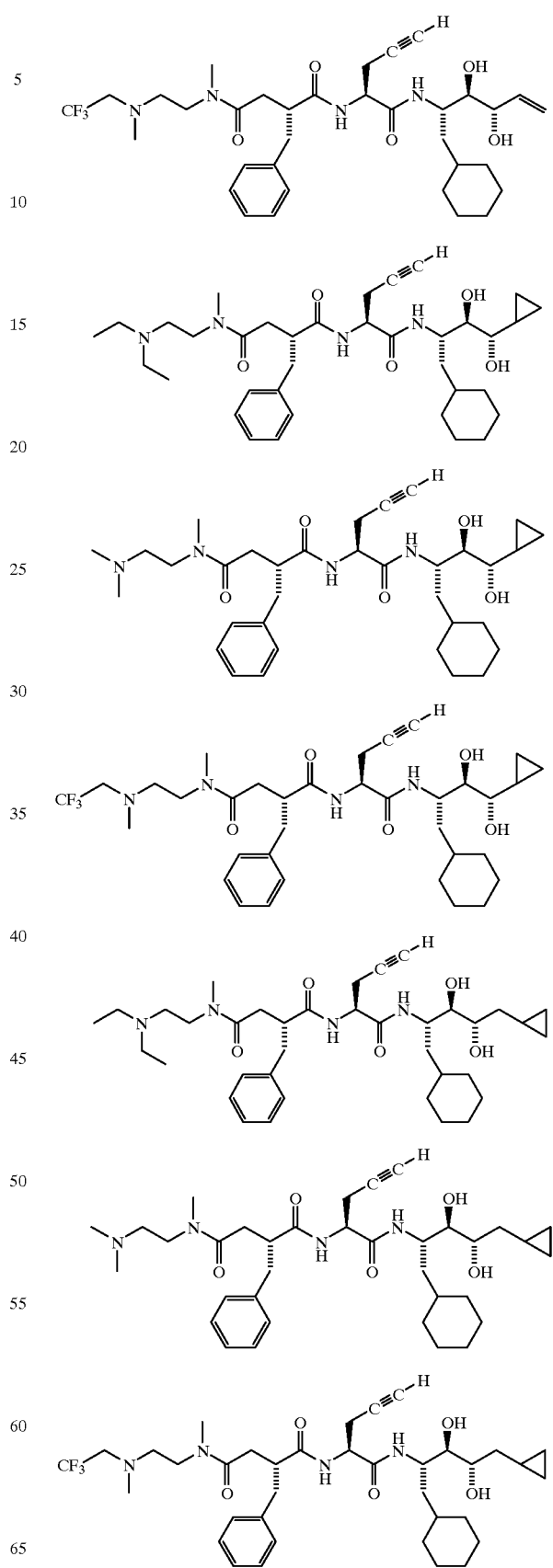

-continued

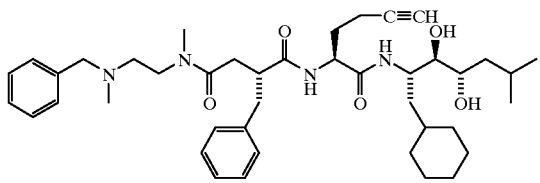

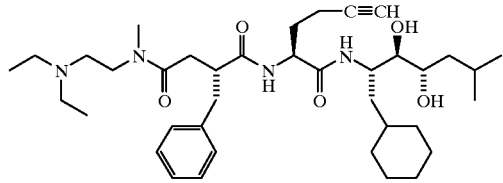

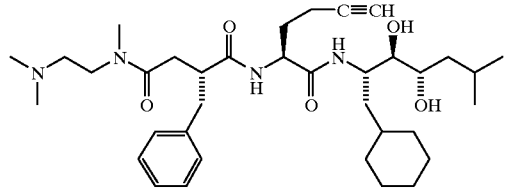

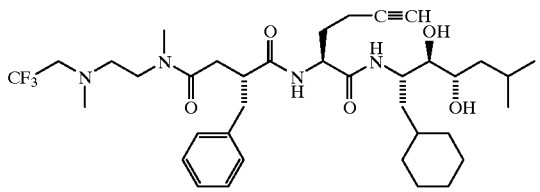

and

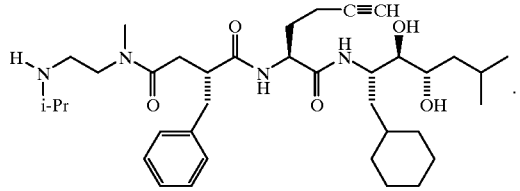

8. The method of claim 6 wherein said compound is N1-[1R*-[[[1S,1R*-(cyclohexylmethyl)-2S*,3R*-dihydroxy-5-methylhexyl]amino]carbonyl]-3-butynyl]-N$_4$-[2-(dimethylamino)ethyl]-N4-methyl-2S*-(phenylmethyl) butanediamide or a pharmaceutically-acceptable salt thereof.

9. The method of claim 6 wherein said compound is [1R*-[[[1R*-[[[1S,1R*-(cyclohexylmethyl)-2S*,3R*-dihydroxy-5-methylhexyl]amino]carbonyl]-3-butynyl]amino]carbonyl]-2-phenylethyl)[2-(dimethylamino)ethyl]methylcarbamate or a pharmaceutically-acceptable salt thereof.

10. The method of claim 6 wherein said compound is [1R*-[[[1-[[[1S,1R*-(cyclohexylmethyl)-2S*,3R*-dihydroxy-5-methylhexyl]amino]carbonyl]-3-butynyl]amino]carbonyl]-2-phenylethyl][2-(dimethylamino)ethyl]methylcarbamate or a pharmaceutically-acceptable salt thereof.

11. The method of claim 6 wherein said compound is

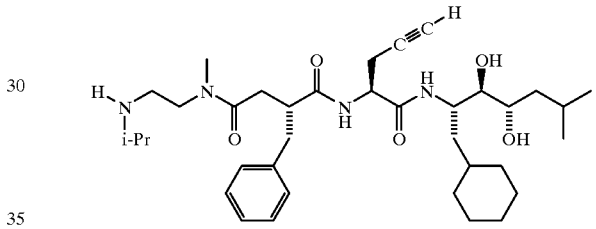

or a pharmaceutically-acceptable salt thereof.

\* \* \* \* \*